US011324603B2

(12) United States Patent
Rebolledo Berrios

(10) Patent No.: US 11,324,603 B2
(45) Date of Patent: May 10, 2022

(54) ANNULAR ASSISTANCE DEVICE

(71) Applicant: Hernan Rebolledo Berrios, Punta Arenas (CL)

(72) Inventor: Hernan Rebolledo Berrios, Punta Arenas (CL)

( * ) Notice: Subject to any disclaimer, the term of this patent is extended or adjusted under 35 U.S.C. 154(b) by 309 days.

(21) Appl. No.: 16/477,500

(22) PCT Filed: Jan. 15, 2018

(86) PCT No.: PCT/CL2018/050005
§ 371 (c)(1),
(2) Date: Jul. 11, 2019

(87) PCT Pub. No.: WO2018/129630
PCT Pub. Date: Jul. 19, 2018

(65) Prior Publication Data
US 2020/0121468 A1   Apr. 23, 2020

(30) Foreign Application Priority Data
Jan. 16, 2017   (CL) .................................. 107-2017

(51) Int. Cl.
*A61F 2/44*   (2006.01)
*A61F 2/46*   (2006.01)
*A61F 2/30*   (2006.01)

(52) U.S. Cl.
CPC ............ *A61F 2/442* (2013.01); *A61F 2/4611* (2013.01); *A61F 2002/3009* (2013.01); *A61F 2002/30069* (2013.01); *A61F 2002/30092* (2013.01); *A61F 2002/3093* (2013.01); *A61F 2002/30133* (2013.01); *A61F 2002/30593* (2013.01); *A61F 2002/30879* (2013.01); *A61F 2002/4615* (2013.01); *A61F 2002/4635* (2013.01)

(58) Field of Classification Search
CPC .............. A61F 2/442; A61F 2002/4435; A61F 2002/444
See application file for complete search history.

(56) References Cited

U.S. PATENT DOCUMENTS

| 4,863,477 A | * | 9/1989 | Monson .................. A61F 2/442 623/17.12 |
| 5,702,451 A | | 12/1997 | Biedermann et al. |
| 6,019,793 A | * | 2/2000 | Perren ..................... A61F 2/442 623/17.16 |

(Continued)

FOREIGN PATENT DOCUMENTS

| AU | 2002243270 B2 | 3/2006 |
| ES | 2208569 T3 | 6/2004 |

(Continued)

OTHER PUBLICATIONS

International Search Report and Written Opinion for related International Application No. PCT/CL2018/050005, dated May 11, 2018; English translation of ISR provided; 19 pages.

*Primary Examiner* — Matthew J Lawson
(74) *Attorney, Agent, or Firm* — Procopio, Cory, Hargreaves & Savitch LLP

(57) ABSTRACT

The present invention relates to a discal annular assistance device and the surgical instruments necessary for the insertion and removal thereof. This new device assists the annulus fibrosus following the exeresis of the nucleus pulposus of a lumbar intervertebral disc, to stop accelerated progression towards the discoligamentous instability of a vertebral unit operated on for a nucleus pulposus hernia.

25 Claims, 37 Drawing Sheets

(56) References Cited

U.S. PATENT DOCUMENTS

| | | | |
|---|---|---|---|
| 6,375,681 B1 | 4/2002 | Truscott | |
| 9,480,574 B2 | 11/2016 | Lee et al. | |
| 2004/0044412 A1* | 3/2004 | Lambrecht | A61F 2/4611 623/17.16 |
| 2005/0004671 A1 | 1/2005 | Ross et al. | |
| 2006/0149380 A1* | 7/2006 | Lotz | A61F 2/30907 623/17.12 |
| 2006/0247655 A1* | 11/2006 | Francis | A61F 2/4611 606/99 |
| 2007/0010889 A1* | 1/2007 | Francis | A61F 2/442 623/17.16 |
| 2007/0021835 A1* | 1/2007 | Edidin | A61F 2/4611 623/17.12 |
| 2007/0233245 A1* | 10/2007 | Trieu | A61F 2/4611 623/17.11 |
| 2008/0195210 A1* | 8/2008 | Milijasevic | A61F 2/441 623/17.16 |
| 2008/0312743 A1* | 12/2008 | Vila | A61F 2/4465 623/17.16 |
| 2010/0256766 A1* | 10/2010 | Hibri | A61F 2/442 623/17.16 |
| 2011/0270399 A1* | 11/2011 | Yurek | A61F 2/441 623/17.16 |
| 2012/0277869 A1 | 11/2012 | Siccardi et al. | |
| 2015/0230929 A1* | 8/2015 | Lorio | A61F 2/447 623/17.16 |
| 2016/0120654 A1* | 5/2016 | Hibri | A61F 2/441 623/17.12 |
| 2016/0361177 A1* | 12/2016 | Biedermann | A61F 2/4611 |
| 2020/0281739 A1* | 9/2020 | Jimenez | A61F 2/442 |
| 2021/0083887 A1* | 3/2021 | Lu | H04L 9/3278 |

FOREIGN PATENT DOCUMENTS

| | | | | |
|---|---|---|---|---|
| WO | WO 2005/089679 | * | 9/2005 | |
| WO | WO-2005089679 A1 | * | 9/2005 | A61F 2/442 |

\* cited by examiner a)

a')

ANNULAR ASSISTANCE DEVICE

CROSS-REFERENCE TO RELATED APPLICATIONS

The present application is a U.S. National Stage entry of PCT Application No. PCT/CL2018/050005, filed Jan. 15, 2018, which claims priority from Chilean patent application CL 107-2017 filed on Jan. 16, 2017, the content of each of which is hereby incorporated by reference into this application.

FIELD OF APPLICATION

The present invention defines a discal annular assistance device and the necessary surgical instruments for its insertion and for its removal. This annular assistance device is an implant that is inserted into the intervertebral space, immediately after a nucleus pulposus removal surgery, with the objective of assisting the remaining disc tissue in order to preserve the anatomy and stabilize the compromised spinal unit, reducing the progression of its postoperative incompetence.

The implementation of this annular assistance device also serves as a reservoir for the administration of biologically active products. In its working position it also prevents the migration of residual disc material to the spinal canal.

BACKGROUND OF THE KNOWN IN THE MATTER

Spinal pain is considered one of the most important public health problems in the industrialized world, showing sustained growth in recent decades. Lesions of the intervertebral disc of the lumbar spine are the most common cause of chronic spinal pain, so there is an incessant global search for new technologies, in the field of implants, with the intention of finding a solution to the enormous group of affected patients.

In the United States of America alone, about 28% of the workforce has experienced disabling low back pain during some period of their career. Of this group, approximately 8% will reach a level of disability status for a period of not less than one year. These patients represent about 40% of the total working hours lost annually in said country, a fact that accounts for a cost that exceeds 25 billion dollars per year.

An intervertebral disc is a complex fibrocartilaginous structure, classifiable as a symphysis, which behaves as a stabilizing and buffering element between two adjacent vertebrae. This morpho-functional set is known as Spinal Unit.

From the structural point of view, it is possible to understand an intervertebral disc as consisting of three parts, namely:
1. Fibrous Rind (Annulus fibrosus): Outer ring of the disc, which is composed of 10 to 12 concentric layers of fibrocartilaginous composition called lamellae. The arrangement of type I collagen fibers, predominant in this portion of the disc, is perpendicular between adjacent lamellae. This structure is reinforced in the anterior and posterior face by the anterior and posterior vertebral common ligaments, respectively. The ring is a container for the nucleus pulposus.
2. Nucleus Pulposus: It is located inside the disc, contained by the fibrous ring and in a discreetly eccentric position towards its back. Normally, the nucleus pulposus consists of a highly hydrated gelatinous matrix, with little cellularity and with a protein constitution strongly represented by proteoglycans and collagen, predominantly of type II. Both the distribution of water and the transit of low molecular weight solutes, such as glucose, or ions such as sodium and calcium, have a strong dependence on the negative electrostatic charge of proteoglycans in their transit through the nucleus. As for collagen, it defines the frame in which chondral cells and proteoglycans are organized. Molecularly, a large number of promoters of the nuclear formation that do not participate in the immunological tolerance process have been described, and for the same reason, are potentially generators of an intense immuno-inflammatory response when exposed outside the boundaries of the fibrous ring.
3. Two disc platforms, of dense hyaline cartilage and concave surface, fix the intervertebral disc to the bony platforms of adjacent vertebrae.

As they degenerate, the intervertebral discs show a loss of height and volume as a result of the progressive reduction of water contained in the extracellular matrix in the nucleus pulposus; this, as a direct consequence of the decrease in proteoglycans synthesis. Taken to a timeline, this phenomenon begins on the disc platforms just before the rest of the disc.

Concomitant with the reduction of proteoglycans, there is a reduction in the synthesis of collagen, namely, the most abundant intervertebral disc protein, this as a consequence of an increased activity of degrading enzymes called metalloproteases.

Collagen lysis appears to be strongly related to the genesis of fissures and tears in the ring.

Recently, the progression of disc degeneration phenomena has also been linked to a decrease in chondral cellularity mediated by apoptotic phenomena.

Several microstructural changes can be verified as degenerative phenomena progress. The nucleus pulposus becomes less viscoelastic and consequently more rigid; in this way, its elastic modulus differs less and less from the structure of the fibrous ring while losing its laminar architecture and weakens in a centripetal progression pattern.

As the disc ring loses resistance, the perimeter of the disc is deformed, and it gradually loses its container capacity and may eventually generate a herniation of the nucleus pulposus.

The progression of disc degeneration causes the separation of the disc platforms from the subchondral bone, facilitating the entry, within the degenerated intervertebral disc, of unidentifiable vascular elements in a healthy disc. As this process progresses, it is possible to find cells of inflammatory nature inside the disc whose phlogistic activity will lead to an increase in proteoglycan lysis proteins and collagen.

According to the doctrines of Kirkaldy-Willis and Farfan (Kirkaldy-Willis W H, Farfan H F: "*Instability of lumbar spine.*" Clin. Orthop. Rel. Res. 1982; 165: 110-23) the process of aging or degeneration of the human lumbar spinal unit can be understood in three successive stages. In this phenomenal description, the anatomical structure of the spinal unit is conceived as a tripod, with a ventral joint, represented by the intervertebral disc and two posterior joints called zygapophyseal joints.

In a first stage, of dysfunction, the characteristic phenomenon is the progressive dehydration of the disc with a reduction of its resistance to the axial load and the progressive transfer of these loads to the posterior pillar of the column. This mechanical insult will trigger an intra-articular inflammatory response in the zygapophyseal joints.

In a second stage of instability, an important loss of disc height can be seen, and consequently, a deformation or bulging of its perimeter. This phenomenon accelerates a greater and progressive overload of the zygapophyseal joints leading to a vertical subluxation of their facets. At this stage, concomitant with the overload of the posterior pillar, a degeneration of the ligament apparatus of the spinal unit is observed, and finally, a loss of sagittal stability and dynamic canal stenosis. Said stenosis is especially evident with the extension movements in the extension of the lumen, a position in which the phenomenon is usually referred to as soft stenosis.

In a third stage, the overload of facet joints leads to the formation of osteophytes, in an attempt to stabilize the spinal unit by increasing contact surfaces. The increase in joint volume will have an impact on the diameters of the canal, which is known as hard stenosis. The progressive deterioration, both of the structure of the disc and of the ligamentous apparatus of the spinal unit, can eventually lead to static instability with listhesis, rotary subluxation, or alterations of the coronal alignment. As a consequence of the above, the spinal unit is pushed to a progressive reduction of the diameters of the spinal canal in the affected segment.

However, clinical practice shows that the appearance of herniations of the nucleus pulposus in any of the degenerative stages described above, the vast majority of disruptive lesions of the fibrous ring which will progress towards the herniation of the material of the nucleus of the disc, are correlated strongly with the initial phases of the degenerative phenomenon.

Although the stages described by the studies by Kirkaldy-Willis and Farfan—at the end of the 1970s—remain entirely valid nowadays, the idea that chronic low back pain, coming from the intervertebral disc, was an independent clinical entity in stages prior to the deformation of the disc perimeter, is relatively recent. Its incorporation into the current state of the art has gained momentum from the studies of Bogduk and collaborators based on the description and characterization of what Crock baptized in the 1980s as internal disc disruption (Bogduk N, Mc Guirk B: *Causes and sources of chronic low back pain*. In Bogduk N, editor: *Medical management of acute and chronic back pain: an evidence-based approach: pain research and clinical management*, Amsterdam, 2002, Elsevier Science BV, pp 115-126). In this regard, Bogduk indicates that "different and independent techniques point to the same conclusion. The internal disc disruption has a distinctive morphology that correlates strongly with spinal pain, for no other cause of low back pain have such multiple and strong correlations been demonstrated."

This condition is a predecessor of the formation of a hernia of the nucleus pulposus. As a tear of the fibrous ring occurs, which weakens it sufficiently and exceeds its restoration mechanisms, the conditions conducive to the progression of nuclear material to the outside of the disc will be created, through this structural weakness of the ring. Thus, pushed by the internal pressure of the disc, the nuclear material will exceed the anatomical limit of continence of the disc perimeter, defined by the fibrous ring, originating a herniated nucleus pulposus.

The herniations of the nucleus pulposus of an intervertebral disc can be subdivided into those that progress vertically through the platforms and into the subchondral bone (known as Schmorl Hernias), and those that are oriented horizontally and more commonly towards the posterior sector of the disc. In this case, the hernial material will occupy space inside the spinal canal, compromising its complacency and giving way to the appearance of compression pain and inflammatory irritation of the neural structures contained therein. Taken to this limit, the critical occupation of the canal and/or the exposure of nuclear material inside translate into a painful condition of the lumbar spine, with indication of surgical resolution, more common in the activity of a spinal surgeon.

The concepts of degenerative progression proposed by Kirkaldy-Willis and Farfan are fully understood to apply to the deterioration of the competence of the spinal unit after a nucleus discectomy.

Under the conception proposed by these authors, the most important structure for maintaining the stability of a spinal segment is the intervertebral disc itself.

In this way, it is possible to understand how, after the removal of the nucleus pulposus from an intervertebral disc, the space occupied by the nucleus pulposus, left to its free evolution, is progressively reduced, as the annular remainder of the intervertebral disc becomes incapable of tolerating the effects of axial load by itself. This annular incompetence leads to the rapidly progressive approach of the disc platforms adjacent to the intervertebral disc, the overload of the posterior pillar, and an acceleration of the degenerative cascade on the spinal unit. This will progress inexorably towards segmental instability and towards the loss of sagittal balance.

The acceleration of the degenerative phenomena of a human lumbar spinal unit as a result of the alteration of segmental spinal geometry and biodynamics, after resection of the nucleus pulposus has been demonstrated in the famous works of R. B. Dunlop, M. A. Adams and W. C. Hutton, in the 1980s (Dunlop R. B., Adams M. A., Hutton W. C. *Disc space narrowing and the lumbar facet joints; The Journal of Bone and Joint Surgery*: vol 66-8, No. 5, November 1984). The reduction of the post discectomy disc height will generate a greater and abnormal distribution of the loads on the zygapophyseal joints, which are designed only to limit the axial rotation. When overloaded, they will degenerate abruptly, causing an important limitation due to pain. In an attempt to achieve the fusion between the two vertebrae of the affected spinal unit and reach a new state of stability, these joints will increase in volume as a way to maximize contact surfaces. This facet hypertrophy will generate a new problem: the narrowness of the canal (spinal stenosis), and thus, the transition to a new state of stability will entail a reduction in the caliber of the canal.

The global prevalence of herniated discs of the lumbar spine segment is estimated between 1 and 3% of the world's population. Most patients are treated with conservative procedures. It is estimated that less than 15% of the prevalent population will require a surgical procedure before the fifth year of having diagnosed their injury.

It is recognized that the rate of lumbar nucleus pulposus hernia surgery shows notable variations in different countries: 100 cases per 100,000 inhabitants in Great Britain, 200 per 100,000 in Switzerland, and 450 to 900 per 100,000 inhabitants in the USA. A conservative figure of incidence of this condition of the spine, proposes figures close to 50 new cases per 100,000 inhabitants each year. The standard surgical technique for the open resolution of a herniated nucleus pulposus of a lumbar intervertebral disc is known as nucleus discectomy. This procedure seeks to resolve the pain and neurological signs that invalidate the patient by carefully removing the disc material that is abnormally arranged inside the spinal canal, thus freeing the neural structures from the compression and inflammatory irritation that this tissue produces.

As in any other surgical procedure, once the critical space conflict is resolved, the normal anatomy should be restored, a principle that in a nucleus discectomy involves preserving the geometry of the spinal unit, preserving the height of the space that separates the adjacent vertebrae, and restoring the sagittal and coronal balance of the affected segment.

During the last two decades of research and development of spinal bioimplants, the objective of restoring the anatomical normality and dynamic behavior of an intervened intervertebral disc has led to two types of conceptually different solutions:
1. Intersomatic intervertebral fusion implants: which attempt to solve the problem through the sacrifice of segmental mobility and the consequent transformation of the two vertebrae of the affected spinal unit, into a single structure by means of the fusion of the bone of both adjacent vertebrae.
2. Disc prostheses: which try to replace the functions of an intervertebral disc or part of the same.

With indications reduced to very particular preoperative spinal conditions, the lumbar prosthetic intervertebral discs have not demonstrated to overcome the results obtained by stabilizing the affected spinal units through intervertebral fusion. Problems of an economic or technical nature, such as the complexity of their surgical implantation or the resistance of the materials used to the enormous loads to which these structures are subjected, remain unresolved problems.

At present and even in the absence of a "gold standard", the literature describes that intersomatic fusion is the most suitable therapeutic model to solve the problems derived from nontraumatic segmental instability, limiting the progression of the normal degenerative cascade of the human spine as it is performed naturally in the late stages of spinal aging. Intersomatic fusion devices known in the art have been classified according to the surgical access routes necessary for their placement.

Designated by means of their acronyms, the techniques PLIF (posterior lumbar interbody fusion), ALIF (anterior lumbar interbody fusion), TLIF (transforaminal lumbar interbody fusion) and its derivatives, require complex and no less risky dissections, resection of important components of the spinal unit and attached stabilization systems that increase the total mechanical energy provided to the tissues, to the rachis structure itself, and in parallel, morbidity and mortality. Learning curves for surgical execution limit the number of beneficial patients and circumscribe their performance only to highly complex centers and to an elite of specialists. Finally, the high cost of both the implants and the complex surgical procedures for their insertion should be considered.

In this group, and according to the way it is inserted, the implants can be basically divided into two categories:
1. Those that are inserted by screwing;
2. Those that are inserted through their impact on the disc space.

In each category, they can be classified as solids, such as those disclosed in U.S. Pat. Nos. 4,879,915; 4,743,256; 4,349,921 and 4,714,469; or those that have the virtue of stimulating osteosynthesis through their own structure, such as those disclosed in U.S. Pat. Nos. 4,878,915; 4,961,740; 5,015,247 and 5,055,104.

Whether they are manufactured in metals with osteoinductive properties, such as titanium and its alloys, or in polymers with treated surfaces, they all share, as characteristic, the difficulty in their manufacture as they require complex milling, smelting and cutting processes.

In a thorough and recent review of the state of the art, document US 2005/0015151 deserves a specific mention, which defines a device that allows the intervertebral disc to be repaired through its insertion into the herniated area, preventing the reappearance of intervertebral disc material outside its annular margin (recurrence). This device is characterized as a nucleus pulposus prosthesis that is inserted into the intervertebral cavity, which has two interconnecting structural components. Each of these components would be made from an elastic and semi-rigid material, suitable for supporting compression loads. The second structural component is inserted into the first one, thus acquiring the shape of a hollow sphere flattened at the poles that has a central cavity which is accessed by a deformable opening in the component, and an interface to which a rigid rod is connected. The second structural component is substantially a complete sphere, which can pass through a deformable opening connecting with the central cavity, in order to form an elastic block that cannot be ejected from its housing when the prosthesis is subjected to mechanical forces. From this document it can be seen that the device, although it adapts to the cavity of the nucleus pulposus, has a flattened sphere shape that once introduced into the cavity, takes its original form to occupy the space in the intervertebral disc.

BRIEF DESCRIPTION OF THE CONCEPTUAL BASES OF THE INVENTION

It has been possible to develop a new annular assistance device that fulfills the function of assisting the fibrous ring after the removal of the nucleus pulposus of a lumbar intervertebral disc, in order to stop the accelerated progression towards discoligamentous incompetence of a spinal unit operated due to a herniated nucleus pulposus. The function of assisting and not replacing, functionally and structurally, the fibrous ring and the remaining nuclear material, after resection surgery of the herniated nucleus pulposus, defines a novel approach in the field of spinal surgery.

This annular assistance device has a variable geometry in one of its planes, which allows it to enter the disc space and adjust itself to the residual surface of the surgery, only by means of the traction of a closure element, without using impact or screwing techniques or elements. In this way, the amount of mechanical energy contributed to the surgical bed is substantially reduced.

Once armed, the system shows absolute congruence both with the profile of the disc platforms and with the surface of the post-surgical cavity (FIG. 1A; 2; 17 A). In this position, it also defines a container function of biologically active materials that enter the cavity created by the annular assistance device, injected through its closure element, by means of a universal connection.

The operation of the new annular assistance device breaks with some paradigms of the spinal implant industry supported by the points detailed below. In each of them, the differences with the solutions currently available are shown, both in the field of patenting and in the commercialization of the type of spinal bioimplants described above.

Importance of the Annulus Fibrosus

Both in studies of real load and in computer simulations using finite element methods, it has been shown that once the nucleus pulposus of a diseased disc has been removed, the fundamental structure with the capacity of resisting axial loads of the spinal unit, is the fibrous ring.

However, both the prosthetic intervertebral discs and the intersomatic fusion devices attempt to occupy the anatomical space and replace the spatial properties of the most central portions of the disc, giving greater importance to the geometric position of the nucleus pulposus. In the case of intersomatic fusion systems, since 1960, a competent fusion has been possible only if the fusion device occupies and contacts the adjacent vertebrae in an area not less than 30% of the central surface of adjacent vertebral platforms. It should be considered that, on average, the theoretical disc surface of adult patients presents in the lower lumbar region antero-posterior diameters close to 30 mm and transverse diameters of approximately 50 mm, so any implant that wants to comply with this postulate has a problem, due to its size alone, for its insertion through the usual access routes to the intervertebral disc. In fact, it can be considered physically impossible to insert a device of that theoretical size through a 50 mm$^2$ surgical field, which is common to assume in approaches with microsurgical or minimally invasive criteria. All fusion devices reviewed and/or used by the work group, require the resection of an important section, both of the posterior portions of the spinal unit and of the fibrous ring itself for its implantation. Similarly, all prosthetic disc replacement systems warn of the problems that arise if the physical center of the prosthesis is not located as coincident as possible with the geometric center of the intersomatic space. In this exercise, large portions of the anterior aspect of the fibrous ring should be resected.

Therefore, it must be admitted that both disc prostheses and fusion implants are arranged inside the disc space with a centripetal approach, seeking to maximize the occupation of the disc space; this, in total disregard of the fibrous ring which, in not a few examples, must be removed in a considerable part of its perimeter.

Geometry of the Lumbar Intervertebral Disc Platforms

It can be observed in the best accredited digital models for the study of the biodynamic behavior of lumbar spinal units, as well as on the physical basis on which the design of prosthetic and intervertebral fusion systems is based, a simplification of the load transfer calculations with models in which the existence of idealized spinal units is assumed, whose disc platforms are represented as flat surfaces, and in which lordosis is minimal.

Unlike this approach, the present invention supports the idea of considering disc platforms as they naturally are: surfaces of concave geometry, with parabolic sagittal and coronal sections. In this model, considering the anatomical reality, the transfer of loads sectionally emulates the distribution of weight on an arc, that is, with an asymmetric and centrifugal distribution of the same. Under this premise, the loads supported by the disc are predominantly deployed on the inner surface of the fibrous ring, rather than on the geometric center of the disc cavity. It is possible to corroborate this axiom by simply observing the natural design of a vertebra, where the bone density of the fibrous ring implantation area, especially in the paramedian and posterior regions of the lumbar discs, is markedly higher than the observable in the subchondral bone of the geometric center of the vertebral body.

Tomographic measurements confirm radiological density differences of up to one third higher in the subchondral bone of the peripheral region of the platforms compared to those observed in the more central portions of the vertebral body. Taken to the limit, this concept explains why in cases of extreme structural weakness, the disc platforms fracture under axial load in their geometric center, as it is usual to observe in osteoporotic fractures of the human dorsolum bar region.

Based on the idea of reinforcing the spinal unit, after the removal of the nucleus pulposus from its disc, and avoiding the collapse of the intervertebral space, the present innovation settles congruently inside the residual cavity, on the area that is more resistant to axial load, that is, on the inner perimeter of the fibrous ring (FIG. 1A; B).

From the perspective of our implant, developing a competent annular assistance function requires positioning the assistance device with a centrifugal approach. This ideal can be achieved with various geometries. Of those whose feasibility has been evaluated, they have been proved theoretically suitable to consolidate their position in the best way by meeting the following criteria:

1. Congruence with the inner surface of the fibrous ring (FIG. 1 A). Based on this criterion, a configuration geometrically close to a cardioid stands out for its ability to adapt exceptionally to the geometry of the residual disc cavity, post discectomy. The way in which the annular assistance device is deployed over the areas in which the load is distributed naturally, supports it in a self-stable way inside the disc space. This symbiosis between the geometry of the post-surgical cavity in the disc and that of the annular assistance device allows the cavity to assist the annular assistance device and the annular assistance device to assist the residual disc tissue. Mutual assistance works naturally for this morphotype, both in static and flexion extension avoiding the need to incur in additional fixing methods. (FIG. 1 B)

2. Congruence with the geometry of the surfaces of the disc platforms. The parabolic morphology of the contact surfaces of the present innovation confers it the ability to distribute axial loads in an extremely efficient manner, anatomically reinforcing the function of the fibrous ring. (FIG. 2 $c$)

3. The capacity to be inserted through a small annular opening. In relation to this criterion, innovation is characterized by having a variable geometry only in the axial plane, which confers it the ability to deform itself to a desirable minimum. In this way, it can be inserted by a standard annulotomy in a nucleus pulposus hernia surgery, both through the medial and lateral accesses to the pedicle (FIG. 17 A). Being already inserted in the post-surgical cavity, it has the ability to unfold itself to its maximum diameters by means of a closure system that produces the shortening of its major axis (FIGS. 6$a$ and 1$d$). Thus, resection of larger portions of the fibrous ring is unnecessary and the integrity of the bony and ligament elements of the posterior pillar of the lumbar vertebrae is preserved. This quality is essential to reduce the post-operative incompetence of the affected spinal unit, further reducing the risk of requiring an arthrodesis of the segment by means of a posterior fixation.

Preservation of the Viable Disc Tissue

The idea of preserving viable disc tissue meets a central maxim of surgery in any scenario: "primum non nocere". However, in relation to a nucleus discectomy, the impossibility of giving central support from the inside of the residual cavity to the possibly viable nuclear tissue, forces to minimize the risk of hernia reproduction by means of the exeresis or ablation of as much of the nucleus pulposus as possible. On the contrary, the present invention, by containing the internal margin of the remaining nuclear tissue, allows a conservative resection of the nuclear material. This procedure could be understood as favoring the preservation of disc material, as a means of revitalizing the intervertebral disc. This way of understanding the technique has special relevance in cases of herniated nucleus pulposus in young patients.

The review of academically reliable information has not resulted in works capable of defining, with a high level of evidence, the phenomena that underlie the healing process of the inner perimeter of the fibrous ring after the removal of the nucleus pulposus in a herniation. However, it is possible to suggest that, given the resistance to displacement of the disc material by a foreign and biologically inert material, as in other similar processes of body scarification, e.g. breast prostheses, the formation of a fibrous capsule that could adhere to the implant by proper treatment of its surfaces can be expected.

Anatomic Adaptation Through Flexibility

As mentioned before, it is characteristic of implants for intersomatic fusion to try to maximize the intervertebral contact from the center of the disc space, a concept in which the ideal structural rigidity should approach that of the elastic modulus of human bones. However, very high values of this variable, result in a high probability of subsidence (implant embedding in the bone of the underlying platforms). On the other hand, very low values can precipitate fatigue and rupture of the material used, which can result in a potentially disastrous situation in the case of a fragmented implant in the vicinity of the spinal canal or the retroperitoneum. The idea of rigidifying an implant and arranging it in the central axis of the disc space exempts the fibrous ring from its functions, forcing the transfer of loads through the implant or prosthesis, in an unnatural way. This phenomenon is the greater the lower the congruence of the external surface of the implant itself with respect to the internal edge of the remaining disc, and the greater the height of the diseased disc, since in this case, the greater the height gain, achieved as a function of the implant or prosthesis, the transfer of vertical loads from the upper to the lower vertebra will be privileged through the implant and not the fibrous ring.

From the perspective of the owner of the present invention, the most suitable way to transfer vertical loads from the upper vertebra of the spinal unit is achieved by supporting the fibrous ring, assuming the internal geometry of the intervertebral disc (FIG. 1 A, B). This way of understanding the problem is also based on the internal microanatomy of the intervertebral disc, characterized by the presence of rings of parallel arrangement and centrifugal development that, as they move away from the center of the intervertebral disc, deposit a greater number of cementitious proteins between them. In this way, the value of the elastic modulus of the intervertebral disc becomes greater the more peripherally it is measured, and not vice versa.

The present invention defines this concept geometrically, maintaining a behavior as elastic as possible in the axial plane to support the fibrous ring, without falling into subsidence. This way of understanding the problem of load transfer is totally opposite to what is known in terms of Intellectual Protection. Thus, instead of maximizing the contact between the implant and the geometric center of the disc platforms, the new device seeks to optimize the contact with the internal limit of the residual cavity and with the peripheral bone of the platforms. The innovation presented herein bases its efficiency in its ability to make its geometry more flexible and, consequently, accommodate both to the residual cavity and to the disc platforms. It thus deflects the function of resisting the vertical load on the fibrous ring of the intervertebral disc, and not to the geometric center of the cavity.

The Device as Element of Osteo- and Chondro-Induction

Although the fundamental purpose of this innovation separates it from the need to locate itself as a solid core in the geometric center of the disc space, this new type of device does not exclude the parallel benefits of achieving a contensive ossification core that is close to in this point in the compartment that, in addition, would collaborate with its fixed positioning. This osteoinductive behavior could be achieved by filling its inner cavity with treated materials and surfaces to favor osteoinclusion. The information gathered shows that this is, somehow, the way in which syndesmophytosis naturally occurs as a way, less efficient however, to assist the fibrous ring.

In recent decades, the global biotechnological scenario has shown a remarkable effervescence in the field of the development of osteoinductive molecules. Currently, this activity has shifted to the scenario of chondroinductive molecules. The innovative annular assistance device proposed herein, once inserted, determines a closed and refillable space by means of a conveniently designed access route to this very end. This characteristic also has no parallel in the state of the art in terms of biologically active products. This aspect will acquire an enormous relevance insofar as the world market offers the opportunity to obtain rejuvenating or restorative molecules of the chondral tissue of the disc. (FIG. 5 *a, b*; 7 A, b; 8*b*)

At present, there are no intersomatic implants whose behavior is based on the premises set forth above. As a summary, the proposed innovation defines a new class of devices characterized in that they provide assistance to the fibrous ring. This new family of implants can be placed through the minimally invasive pathways by which the standard exeresis of a herniation of the lumbar spinal segment of the lumbar spine is performed, thus establishing an original concept and behavior, as well as breaking with several paradigms, such as the percentage of minimum contact area between the device and the disc platforms, or the "necessary" rigidity of the implants. Its operation emphasizes the support to a fundamental anatomical structure in the recovery of the spinal unit, as is the fibrous ring, rather than in the replacement of its functions, a situation that involves the transfer of loads from the upper to the lower vertebrae, by an unnatural route, as is the center of the disc space. Finally, it represents an effective container for potential biologically active materials that induce osteo or chondro-induction.

Removal

One of the problems less solved by the market, both for intersomatic fusion implants and for disc prostheses, is the problem of removal. The need to remove any of these devices, in case a complication arises, determines the need to perform major surgery. In these approaches, morbimortalities are usually assumed to be even greater than those of implantation surgery. The present innovation, on the other hand, offers a possibility of removal through the same approach routes used for its placement, using for this purpose an extremely simple instrument.

Material of the Annular Assistance Device

The need to integrate the characteristics of materials resistance with elastic modules similar to bone, but with an elastic and radiolucent behavior, have foreseen the use of materials from the plastics family. Our initial tests have been carried out with PEEK (Polyether ether ketone) and in more recent stages, with PSU (Polysulfones) and SPU (segmented polyurethanes). The use of new biocompatible polymeric materials with shape memory is also considered.

DESCRIPTION OF THE FIGURES

FIG. 1c': Detail view of the upper pole of the semi-rigid ring, focused on the portion of anterior and posterior ribs;

FIG. 1A: Axial section view in of the semi-rigid ring inserted in the disc space, in its spinal unit;

FIG. 1B: Isometric view of the semi-rigid ring contained inside a spinal unit, composed of an intervertebral disc and its adjacent vertebrae;

FIG. 2a': Ventral section view, oriented from the anterior face towards the posterior face;

FIG. 2a": Sagittal section view of the semi-rigid ring, oriented from the proximal pole to the distal pole;

FIG. 2b': Detail view, showing the slight concavity of the interior aspect of the anterior face;

FIG. 2b": Detail view, showing the slight concavity of the inner aspect of the posterior face;

FIG. 4a': Detail view of the posterior support rib of the semi-rigid ring in contact with the upper vertebra;

FIG. 4a": Detail view of the posterior support rib of the semi-rigid ring in contact with the lower vertebra;

FIG. 4A: Axial view of a spinal unit;

FIG. 5b': Detail view of the semi-rigid ring, housing the closure element in its distal pole;

FIG. 5A: Semi-rigid ring with its closure element, oriented in a perspective view towards the anterior face and the distal pole;

FIG. 6a': Detail view of the posterior face and distal pole of the semi-rigid ring, indicating the location of the positioning element;

FIG. 7A: Axial section view of the closure element from its distal to proximal pole;

FIG. 8a': Detail view of the proximal pole indicating the tubular exit hole for the closure element;

FIG. 9a': Detail perspective view of the section with the locking elements of the closure element;

FIG. 10a': Detail view of the proximal pole of the closure element, highlighting the reductions in diameter by section;

FIG. 10b': Detail view of the proximal pole of the closure element;

FIG. 11a': Sagittal section view towards the distal pole of the semi-rigid ring;

FIG. 11c': Detail view of the support rib, with its slot in contact with the closure element;

FIG. 12a': Detail view of the tubular exit hole, in the proximal pole of the semi-rigid ring which is divided into a distal and a proximal portion;

FIG. 12a": Detail perspective view of the distal portion of the tubular exit hole containing the closure system;

FIG. 12b': Detail view, in perspective, of the semi-rigid ring in axial section and the closure element, with the closure system between the closure element and the semi-rigid ring;

FIG. 13a': Axial section view of the semi-rigid ring in its fully assembled state, the number of locks of the closure element is "y";

FIG. 13b': Detail view of the closure element exiting the removal instruments, in the fully assembled state of the semi-rigid ring, the number of projections "y" at the exit of the instrument is greater than "x";

FIG. 14*a*': Axial section view of the proximal pole of the semi-rigid ring, closure element separated by fracture in the distal portion of the tubular exit hole;

FIG. 15*a*': Detail view of the semi-rigid ring, highlighting the two previous perforations for tool pushing and mill drilling;

FIG. 15*b*': Axial section view of the proximal pole and posterior face of the semi-rigid ring, indicating the behavior of the extraction rod when entering through the perforation and unloading the material in front of it;

FIG. 16*a*': Axial view of the semi-rigid ring, with closure element partially inserted in its interior;

FIG. 16*a*": Axial view of the semi-rigid ring, with closure element located completely inside;

FIG. 17*b*': Sagittal section view of the spinal unit with the action of the distal end of the insertion cannula, separating the disc space to a dimension "x", greater than the previous "y" space;

FIG. 17A: Axial view of the surgical instruments, traveling along the route used to resect the lesion of the nucleus pulposus, towards the treated disc, the instruments contain the semi-rigid ring with its closure element and the positioning element;

FIG. 20*a*': Detail view of the disc space proximal to the work hole, the extraction rod breaks the locking element of the tubular exit hole of the semi-rigid ring;

FIG. 20*a*": Axial view of the disc space where the semi-rigid ring is in its minimum space configuration after breaking the closure system, extraction rod is collected by dragging the semi-rigid ring to the extraction cannula;

FIG. 22*a*': Detail view of the distal pole of the pushing cannula, focused on a cross section where the work holes a" and a'" go through;

FIG. 22*a*": Detail view of the distal pole of the pushing cannula with a portion of the closure element located in its work hole;

FIG. 22*a*'": Detail view of the distal pole of the pushing cannula with a portion of the positioning element located in its work hole;

FIG. 25*a*': Detail view of the pushing cannula in its proximal pole having a variation in diameter to serve as a stop in the assembly;

FIG. 25*b*': Detail view of the axial section of the distal pole of the pushing cannula, indicating the configuration of the housing wire to the assembly instruments;

FIG. 26*a*': Detail perspective view of the pushing cannula in sagittal section complemented with the thread of the distal portion of the locking screw where they are screwed;

FIG. 26*a*": Detail perspective view of the locking screw in axial section at its proximal pole, the tubular portion where the twisting lock is housed is indicated;

FIG. 28*a*': Detail view of the distal portion of the insertion cannula, with sagittal section prior to the hem i-ovoid form;

FIG. 28*b*': Detail view of the insertion and pushing cannula set in sagittal section, position of the pushing cannula in its initial position;

FIG. 28b''': Detail view of the insertion and pushing cannula set in sagittal section, position of the pushing cannula in rotation on its axis;

FIG. 30a': View of axial section of the distal portion of the insertion cannula, containing the semi-rigid ring in its minimum space configuration;

FIG. 31b': Sagittal view of the proximal portion of the insertion cannula, indicating the housing of the closure sheet;

FIG. 32a': Sagittal section view of the closure sheet, whose profile fits the space between the insertion and pushing cannulas;

FIG. 32b: Perspective view of the distal portion of the aforementioned assembly, indicating where the closure sheet is positioned between the insertion and pushing cannulas;

FIG. 35a': Detail view of the distal portion of the extraction cannula, it presents a conical section of angle Θ1 beveled at an angle Θ2;

FIG. 35b': Detail view of the distal portion of the extraction cannula, focused on the slot that crosses the entire piece;

FIG. 36a': Detail view of the base of the removal mill, in perspective towards the distal portion, indicating the configuration of the hooks on the base to cling to the semi-rigid ring;

Figure 36:
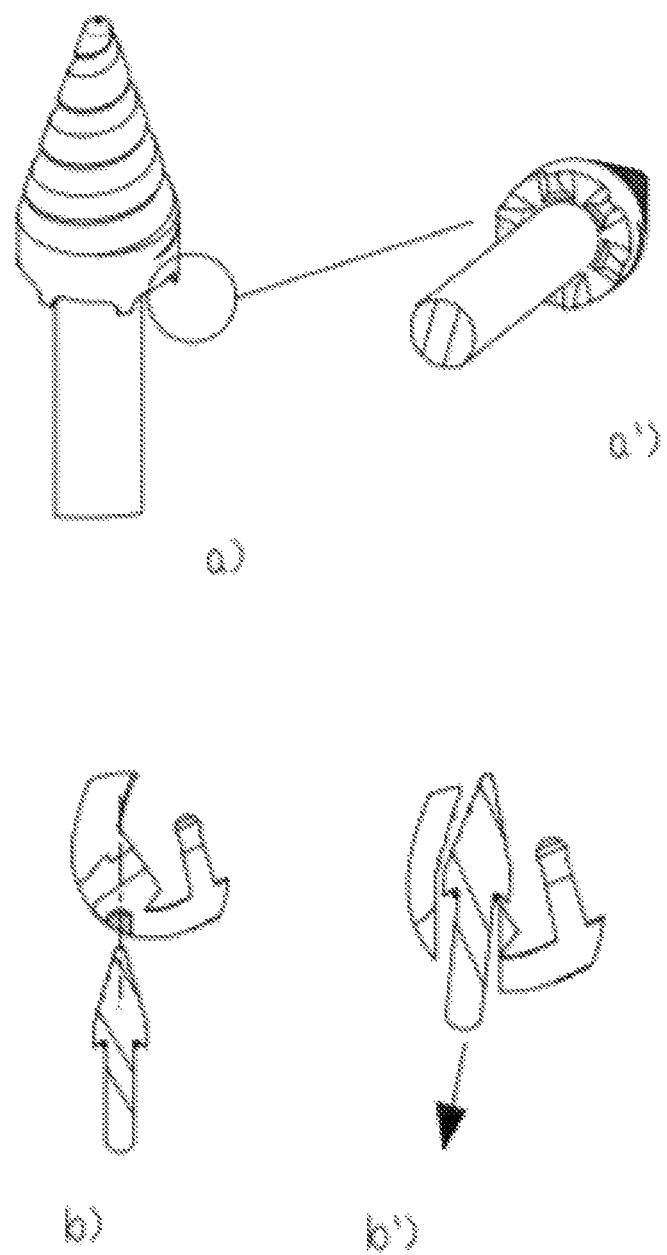
FIG. 36a: Isometric view of the distal portion of the removal rod of the removal instruments.
Figure 37:
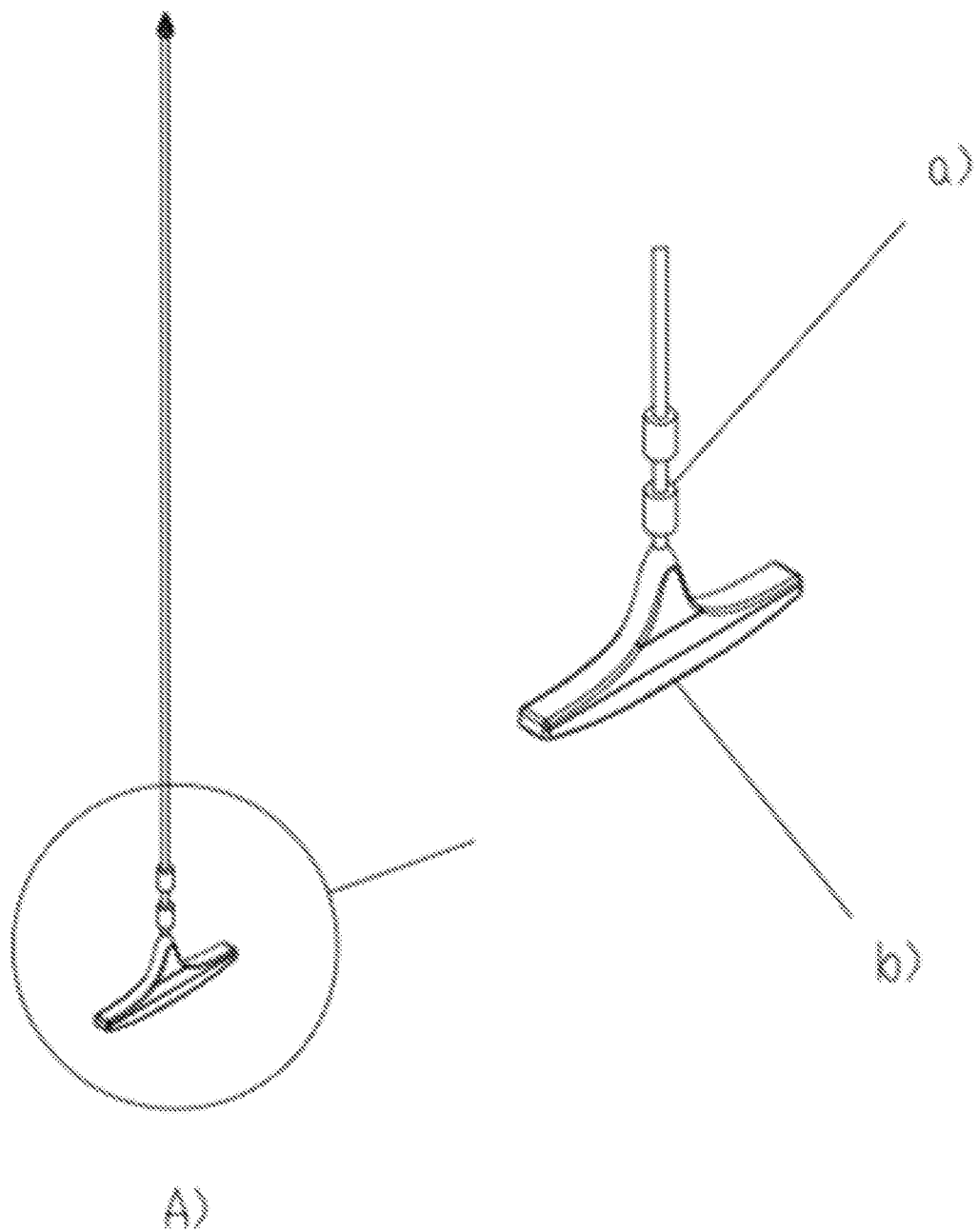

FIG. 36b: Axial section view of the distal portion of the extraction rod in line of action with the hole of the posterior proximal portion of the semi-rigid ring;

FIG. 36b': Axial section view of the distal portion of the extraction rod acting on the scraped region of the semi-rigid ring closure system;

FIG. 37a: Detail view of the proximal portion of the extraction rod, indicating the proximal portion where there is a diameter reduction for hammer handling;

FIG. 37b: Detail view of the proximal portion of the extraction rod, indicating the handle;

FIG. 37A: Isometric view of the removal rod of the removal instruments.

DETAILED DESCRIPTION OF THE INVENTION

To understand the details of the proposed inventive solution, the structure of the device to be implanted is described below, which, based on its functional behavior, we have called the Annular Assistance Device (AAD). The necessary surgical instruments are also detailed, both for insertion and removal, as well as the technique to carry out these procedures.

It is clarified that the morphological description of the device and its instruments is not limited to their dimensions, the spinal level in which it is represented, the type of mechanical behavior, the material used, or the number of elements illustrated.

As deduced from the comments made in the previous paragraphs, the AAD seeks to preserve and/or restore the anatomy of the spinal unit by preserving the height of the space that separates the vertebrae adjacent to a diseased intervertebral disc. This, after the excision of the nucleus pulposus compromised by degenerative pathology or other similar nosopathological situations, in the lumbar segment of the human spine.

Its function is, as a prerequisite, to develop the nucleus discectomy with the least possible impact on the fibrous ring of the diseased disc and on the disc lamellae near it.

Figure 1:
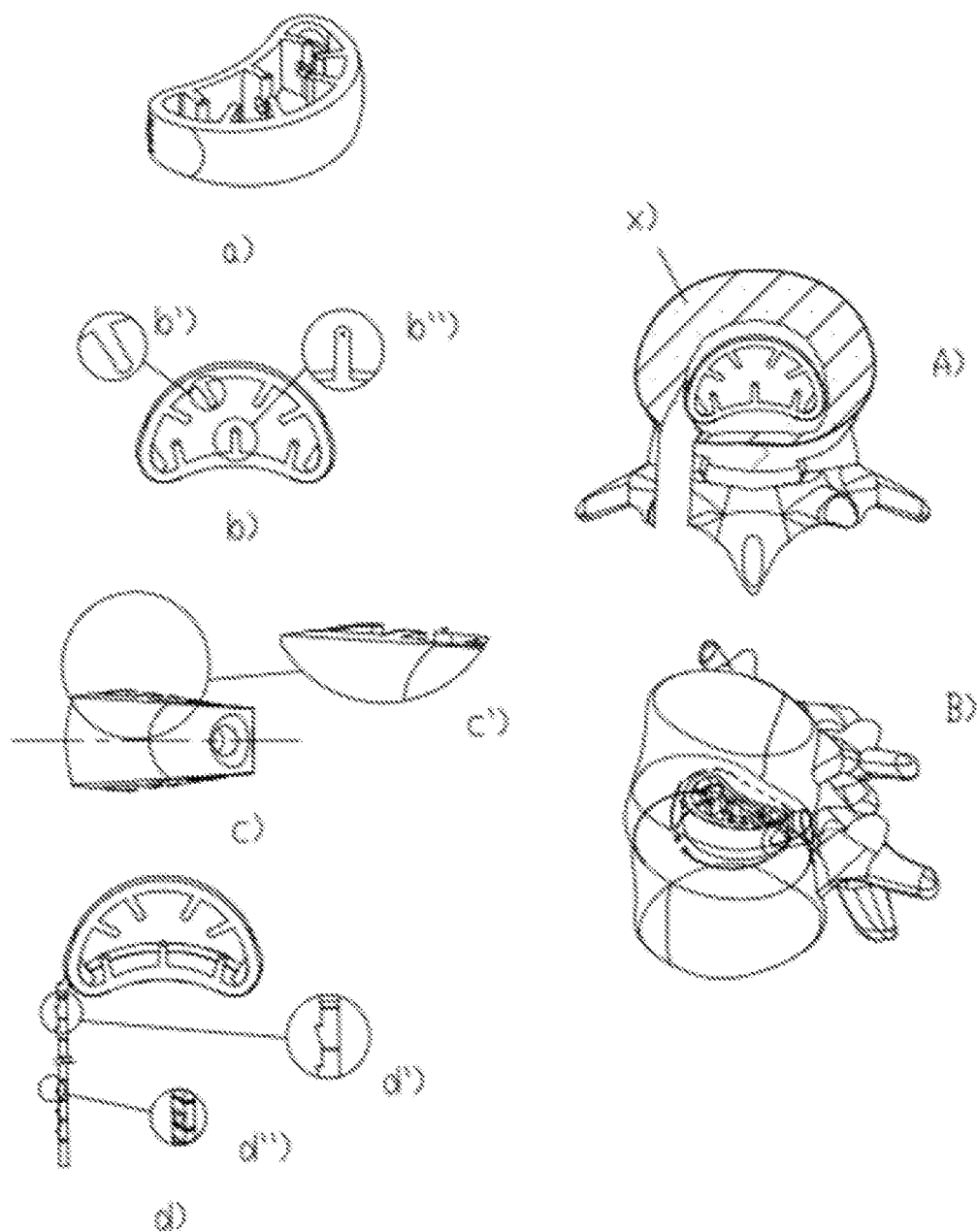
FIG. 1a: Isometric view of the semi-rigid ring.
FIG. 1b: Axial view of the semi-rigid ring with detail in support ribs (b', upper rib; b", lower rib)
FIG. 1c: Sagittal view of the semi-rigid ring.
FIG. 1d: Axial view of the semi-rigid ring with its closure element (d', detail view of locking element, d", detail view of locking elements in proximal pole)
FIG. 1x: Fibrous ring present in the intervertebral disc.

As the figures show (FIG. 1A, 2c), once inserted into the intervertebral space the device is self-contained by a change in its geometry and by an adequate congruence between the same annular assistance device and the limits of the space where it is located, that is, the fibrous ring itself, viable nuclear debris, and both disc platforms. The device is also equipped with a minimum of protrusions that anchor it in its final position (FIG. 1c'; 4a, a', a").

Architecture of the Annular Assistance Device

For the purposes of its description, the definition of distal and proximal has been considered from the perspective of the operator.

In general, the AAD consists of three fundamental elements.

1. A structural element, defined by a semi-rigid ring with asymmetric thickness, which, in the final position, acquires a cardioid shape with convex upper and lower edges in the axial plane (FIG. 1b, c).
2. A closure and securing element, with unidirectional locks, which by means of its traction allows the stabilization of the semi-rigid ring in its final geometric configuration. The closure element also serves as a route for the administration of bioactive materials into the ring cavity (FIG. 1d; 7; 9).
3. A positioning element defined by a strip that is temporarily attached to the distal pole of the semi-rigid ring allowing its manipulation at the time of installation of the AAD This strip, when pulled from one of its ends, is released from the fastening of the semi-rigid ring once it is already armed and arranged in the disc space in its final position. (FIG. 6a, a', b; 14b).

In its working position, the AAD offers its convexity towards the front and its concavity towards the back (FIG. 1b, d, A).

Seen from a sagittal plane, both the upper and lower edges have convex surfaces in congruent opposition to those that, naturally, the disc platforms offer (FIG. 1c; 2c; 11a').

Figure 4:
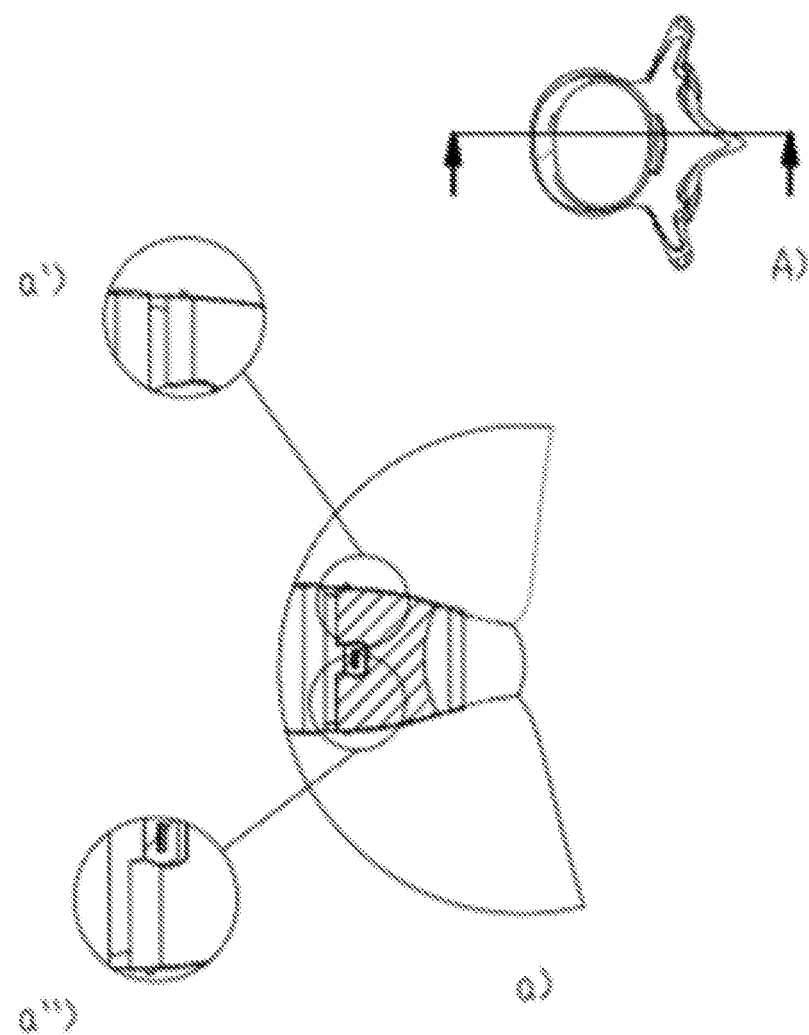
FIG. 4a: Sagittal section view of the semi-rigid ring, contained in its spinal unit, focused on its posterior face.

Support ribs with centripetal orientation are detached from the inner surface of the device, which, as they move away from the variable geometry ring, approach the geometric center of the device (FIG. 1a, b, b', b"). Those that emerge from the posterior portion are characterized by having at their ends spikes of osteoinductive and radiopaque material, to favor the anchorage of the device and its intraoperative visualization under radioscopy, and for showing a slot in the midline of its sagittal section with the morphology necessary to house and secure the closure element of the annular assistance device (FIG. 4a, a', a"; 1a; 5a).

Figure 3:
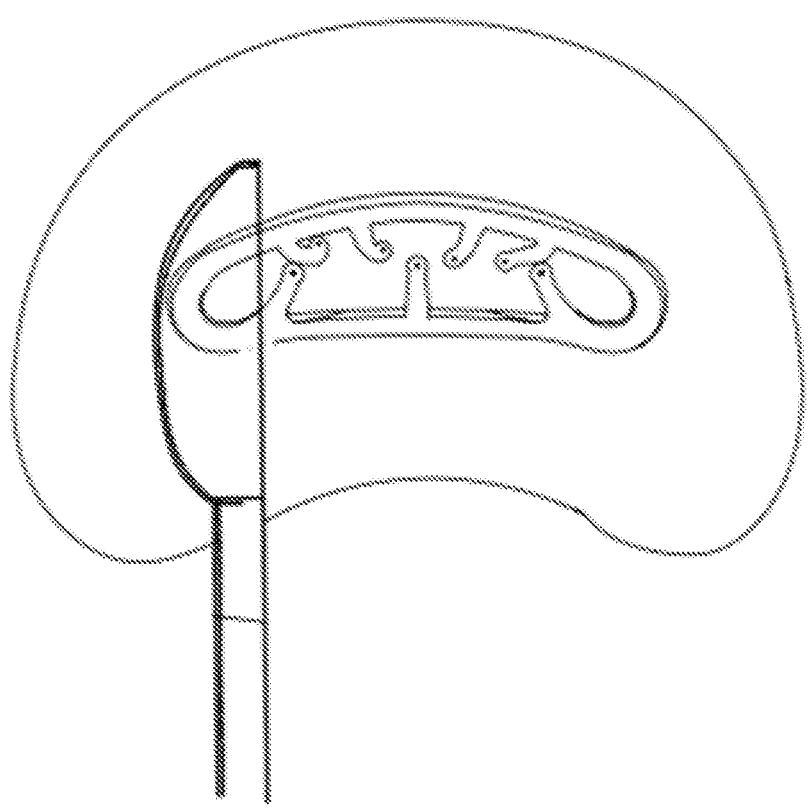
FIG. 3: Axial view of the semi-rigid ring, in a configuration of minimum interior space, inside the intervertebral disc.

These support ribs protrude from the semi-rigid ring with a flexible behavior. In this way, its deprojection is made possible by allowing the deformation of the device to a minimum in the anterior-posterior axis and towards a complete reduction of the space inside the semi-rigid ring, at the moment when it is inserted into the disc space (FIG. 3; 13a; 17A).

In the latero-lateral axis, the points furthest from the annular assistance device represent the place where the closure element of the ring is inserted in the semi-rigid ring. These points, in which said ring also has its greatest thickness, are called poles (FIG. 6a, b; 8a').

Figure 2:
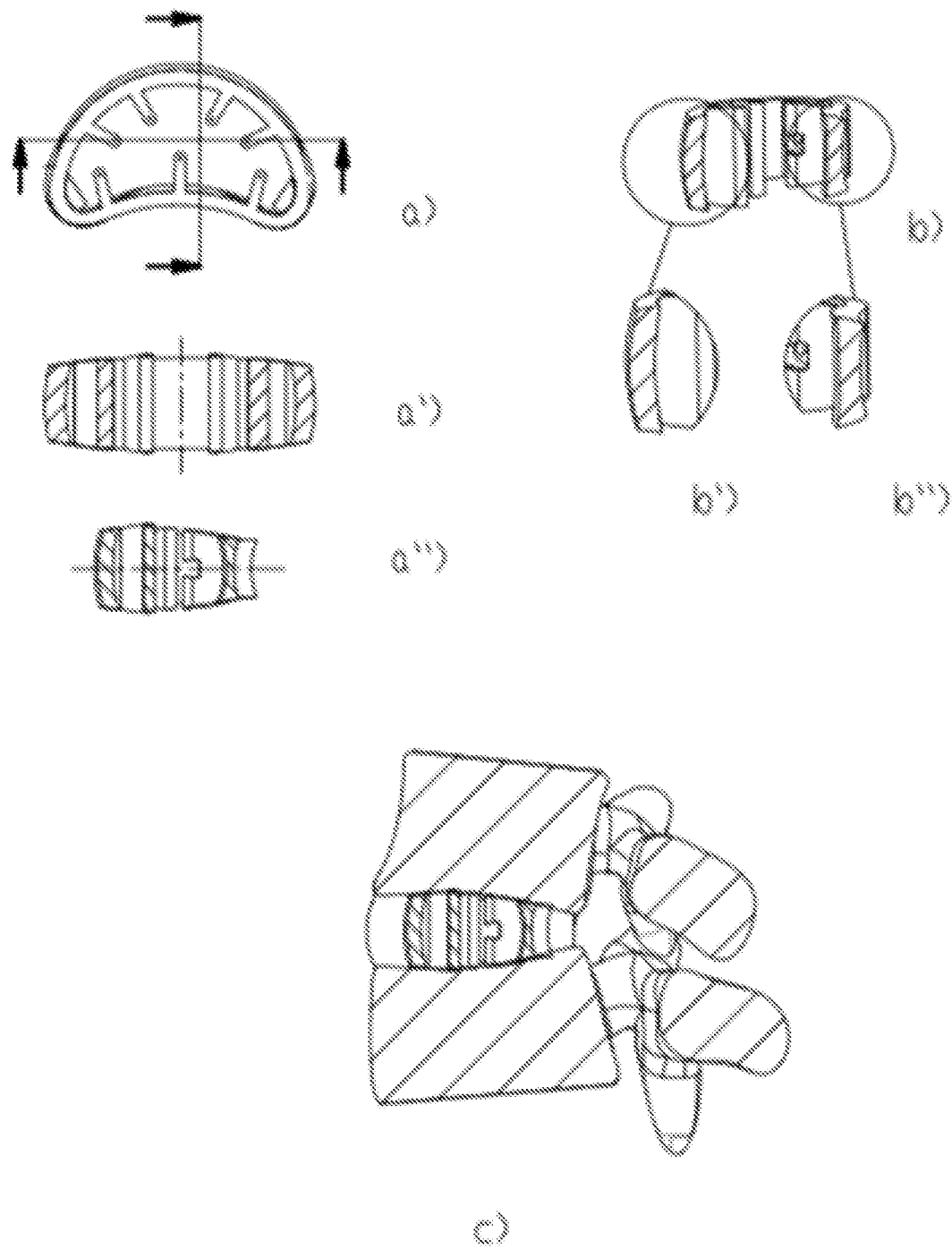
FIG. 2a: Axial view of the semi-rigid ring.
FIG. 2b: Sectional view of the sagittal plane of the semi-rigid ring, oriented in perspective view from the proximal pole to the distal pole.
FIG. 2c: Sagittal section of the semi-rigid ring inside its spinal unit, in the disc space.

The global geometry of the AAD meets symmetry criteria in an axial section plane, which is why the same annular assistance device can be used for both right and left lesions, simply by inverting it (FIG. 2a', a").

The height of the device is equivalent to the height that the diseased disc space offers, depending on: the level of the spinal lesion, age group, gender, and particular conditions of the patient.

In a sagittal medium section, the height of the device will be symmetrical or asymmetrical between the maximum anterior and posterior dimensions, depending on the degree of lordotization required for its adjustment to the disc space post nucleus discectomy. Nevertheless, and only for the purposes of its description, the present exercise represents the device theoretically inserted into a disc of the middle lower lumbar region of a human being (FIG. 2c).

Figure 11:
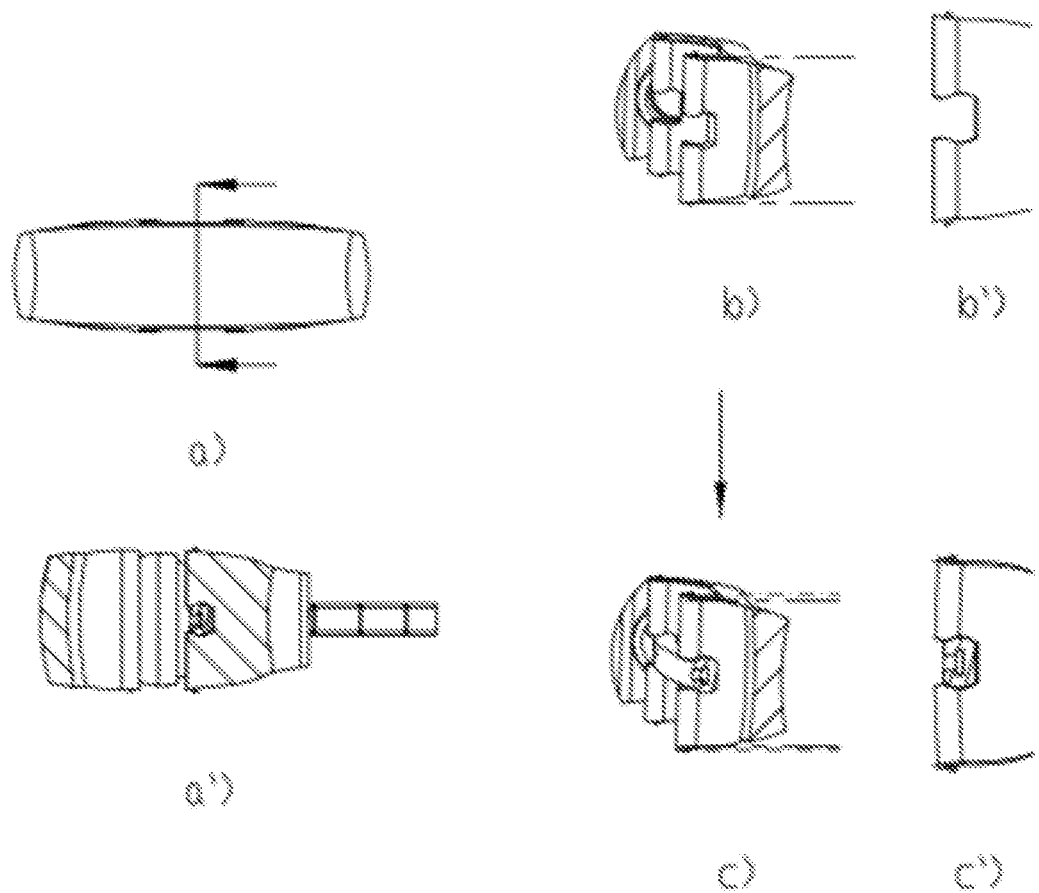
FIG. 11a: Ventral view of the semi-rigid ring towards the anterior face.
FIG. 11b: Detail view of the semi-rigid ring on its posterior face, indicating the securing slots of the support ribs, without the closure element.
FIG. 11c: Detail view of the semi-rigid ring on its posterior face, indicating contact of the securing slots with the closure element.

The maximum average height of the AAD is exceeded only by the spikes at the ends of the posterior support ribs, which will become evident on this limit when closing and securing the device (FIG. 11c, c').

The AAD has a closure element, as shown in the figure (FIG. 1d; 5a, b'; 6a, a'; 7A), which consists of an elongated tubular structure made from a semi-rigid polymer, and that in its closed position brings the poles of the device closer on the transversal major axis of the cardioid.

Figure 16:
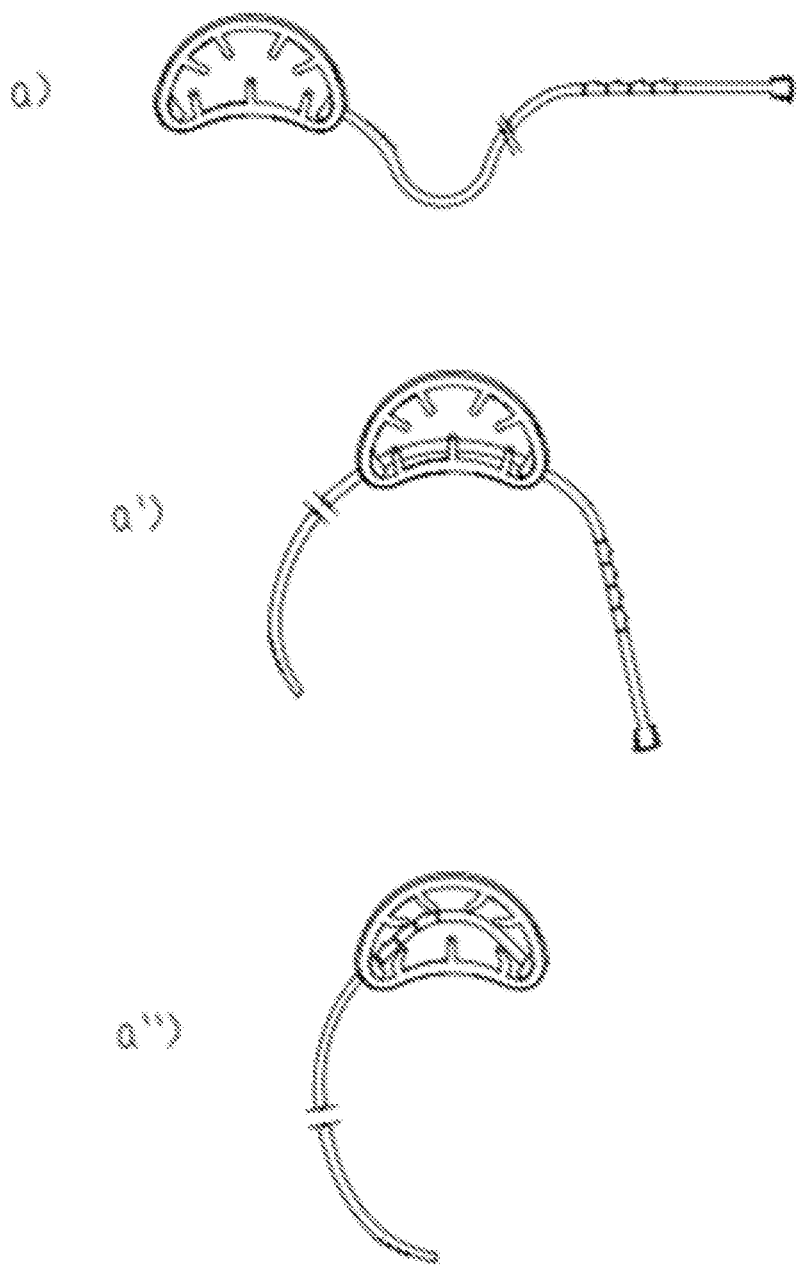
FIG. 16*a*: Axial view of the semi-rigid ring, with closure element at the access of the posterior distal pole.
Figure 17:
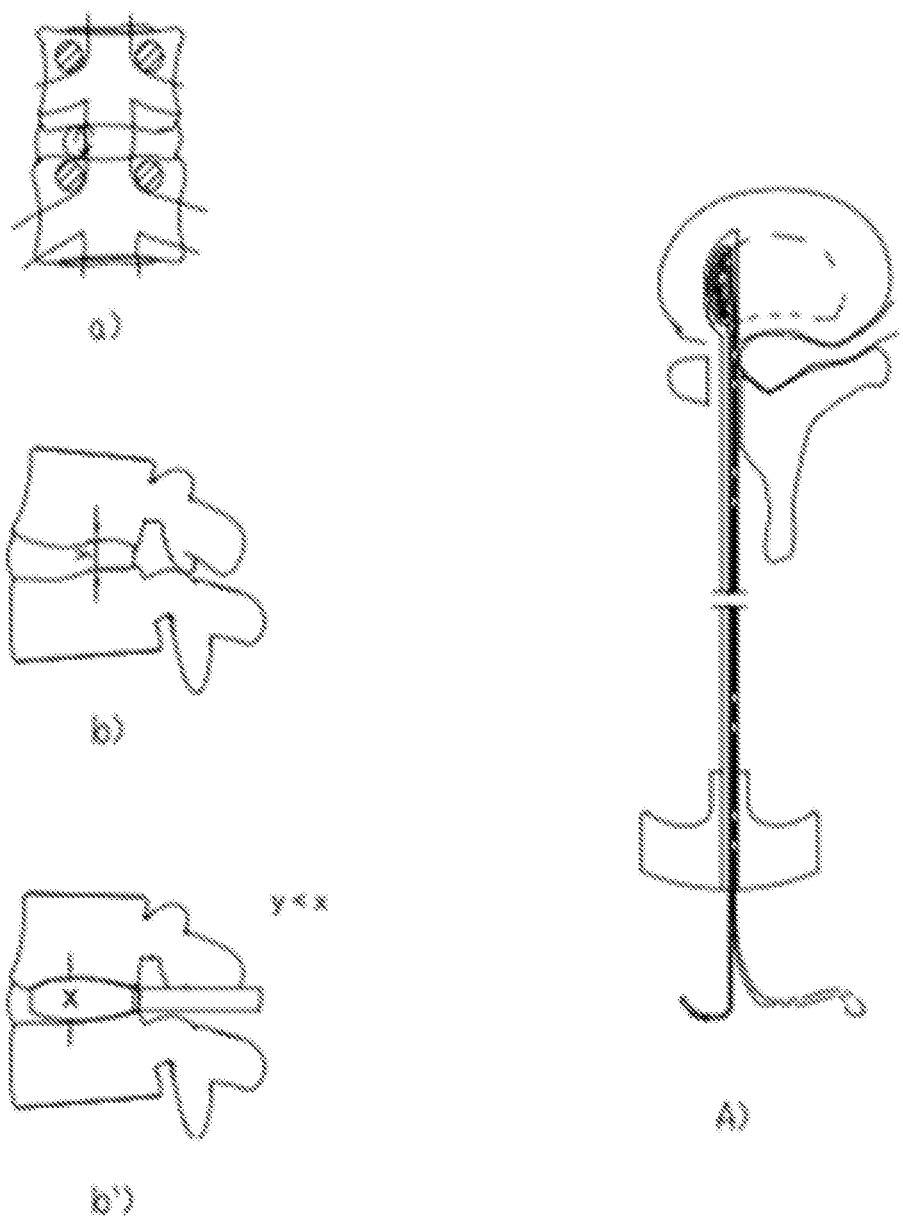
FIG. 17*a*: Ventral posterior view of the spinal unit, indicating the workspace in the vicinity of the neural elements of the spinal canal.
FIG. 17*b*: Sagittal section view of the untreated spinal unit, indicating the height of the disc space "y"
Figure 18:
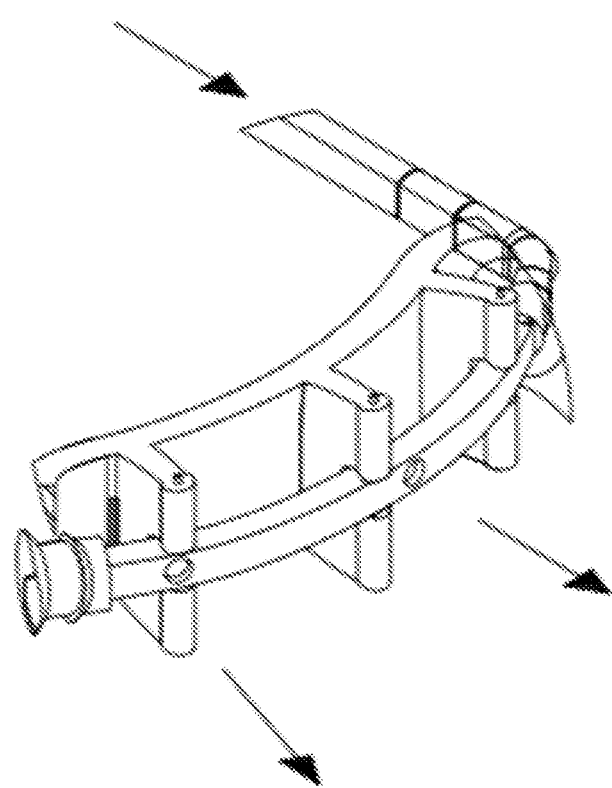
FIG. 18: View of the posterior face of the semi-rigid ring, oriented in perspective towards the distal pole, indicating the behavior of the biocompatible fluid when passing through the middle area of the closure element mounted in the meridian canal, the biocompatible fluid enters through the holes, as indicated by the arrows.
Figure 19:
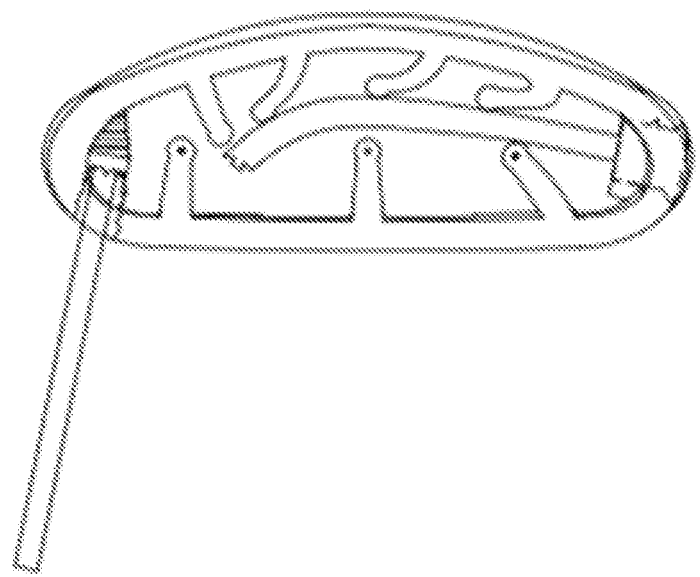
FIG. 19: Axial view of the semi-rigid ring in its two-dimensional position after the closure element is broken.

The closure element is introduced inside the semi-rigid ring of the AAD, prior to its insertion, through an opening and anchor hole, as seen in the figure (FIG. 16a'). The opening and anchor hole is located on the opposite side next to the patient's approach, being the most distal point of the annular assistance device with respect to the operator (FIG. 5b'; 6a, a').

Figure 15:
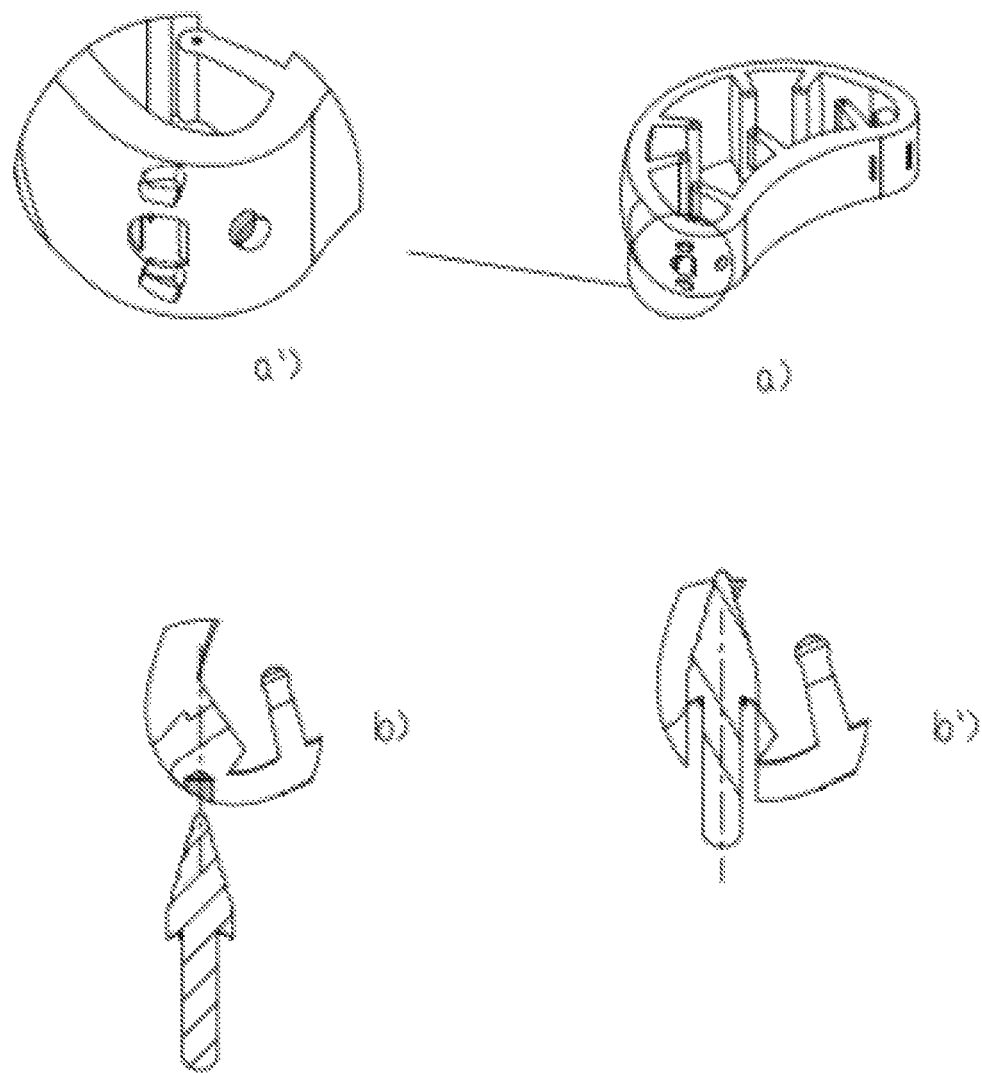
FIG. 15*a*: Isometric view of the semi-rigid ring focused on the proximal pole and posterior face.
FIG. 15*b*: Axial section view of the proximal pole and posterior face of the semi-rigid ring, indicating the perforation for the entry of the extraction rod, line of action on the closure system.

On the surface of the proximal pole of the semi-rigid ring and in relation to the exit hole of the closure element, there are three other perforations, two ventral that serve as support points for the tool for introducing the device, and a posterior one that allows the insertion of the removal instruments of the annular assistance device (FIG. 15a, a'). In the particular case of the posterior perforation, the major axis thereof coincides with the geometric center of the locking ring of the semi-rigid ring (FIG. 15b; 24b). This arrangement allows a perforation guided by this axis to cause the rupture of the locking system of the AAD to promote its disassemble and removal (FIG. 15b, b').

In order to describe the AAD in terms of the structural relationships between its semi-rigid ring and its closure element, it is described as already armed in three designated sections: distal, middle and proximal (FIG. 6a).

Distal Annular Section:

In this section, the semi-rigid ring has an entry hole for the closure element (FIG. 6a, a'; 5b, b'). This hole has a diameter with a small increase in diameter (FIG. 5b), which gives support to the most distal portion of the closure element. The diameter of the perforation is sufficient for the insertion of the closure element and its unidirectional lock. This lock secures the closure element to the semi-rigid ring in the event that it is cut to facilitate the removal of the AAD (FIG. 5b; 19).

Figure 5:
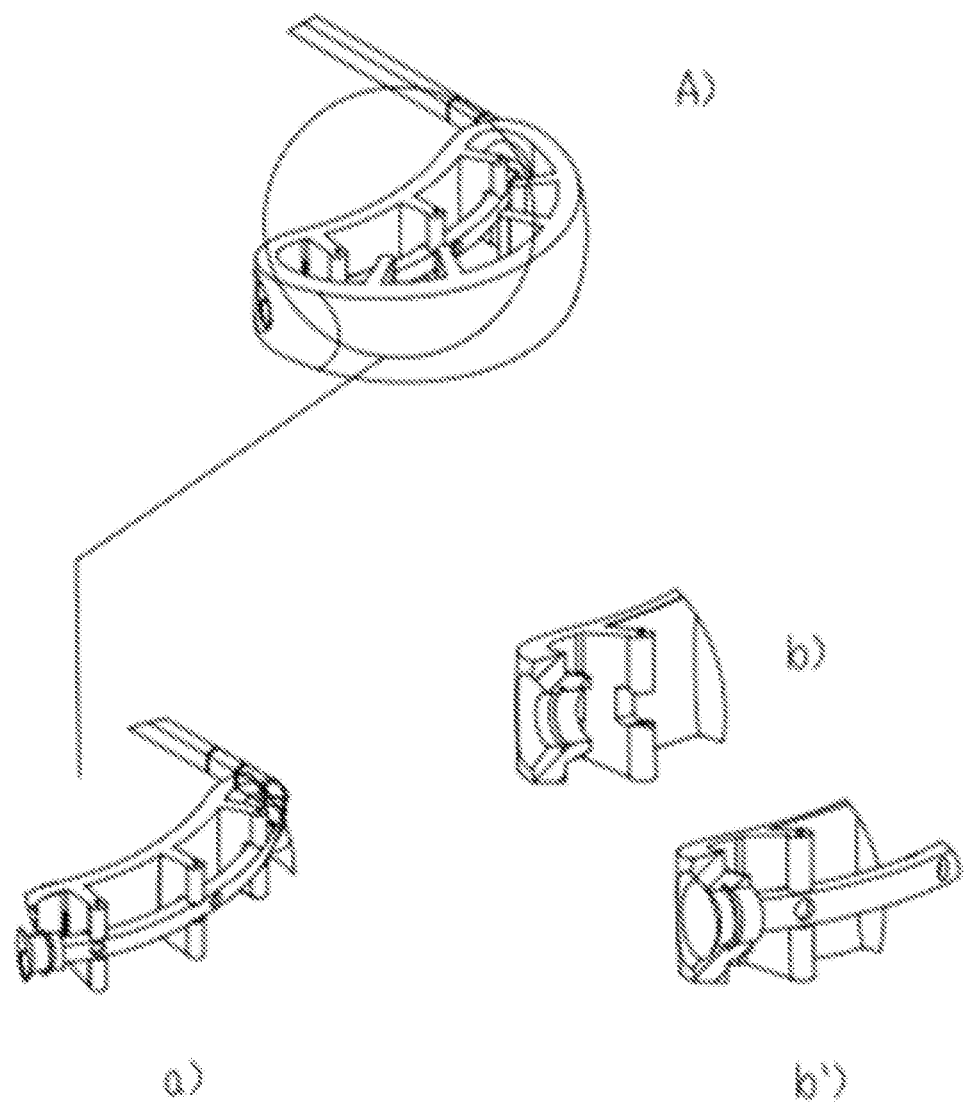
FIG. 5a: Detail view of the inside of the semi-rigid ring with its closure element housed in the securing slots of the posterior support ribs.
FIG. 5b: Detail view of the semi-rigid ring, focused on the access of the distal pole and the posterior support rib with its slot.
Figure 7:
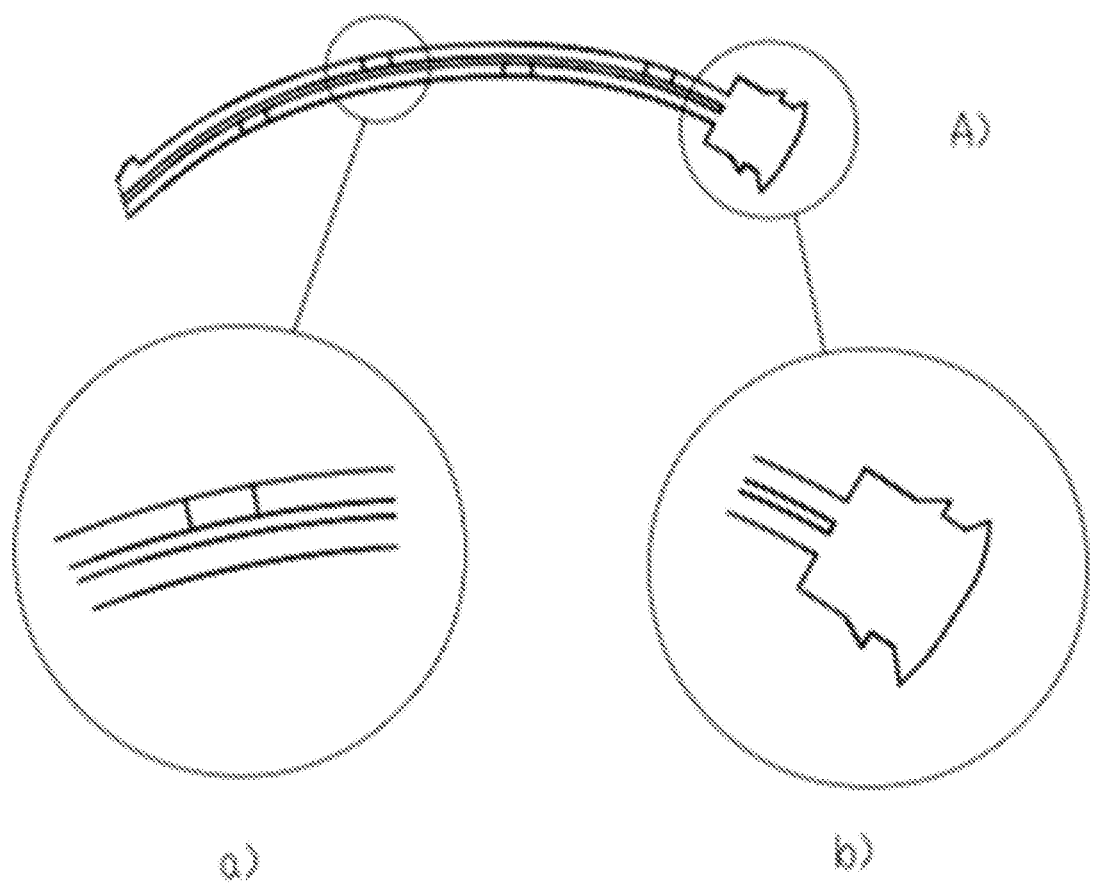
FIG. 7a: Detail view of the closure element showing the hole towards the inside of the semi-rigid ring.
FIG. 7b: Detail view of the closure element indicating the distal pole along with its unidirectional lock.

The closure element has in its most distal portion a conical section congruent with the countersink of the entry hole of the semi-rigid ring, so that once its position is secured it does not distort its surface (FIG. 7b). As described before, it is equipped with a tab that acts as a unidirectional lock (FIG. 5b'). This, which is the strongest portion of the closure element, extends into the semi-rigid ring by means of a tubular section with a coronal section characterized by having its anterior and posterior faces truncated so that the larger diameter corresponds to the vertical plane and the smaller to the horizontal plane. In this section of the closure element a series of perforations that communicate the inner bore of the closure element with the interior space of the AAD can be observed (FIG. 5 a, b'; 6 a, 7 a). The larger diameter of this tubular section of the closure element is coincident with the securing slots of the support ribs arranged on the posterior face of the semi-rigid ring, whose purpose is to fix the closure element to said section of the AAD once it is geometrically stabilized in its working position (FIG. 5 a; 6 a; 11 b, c).

Figure 6:
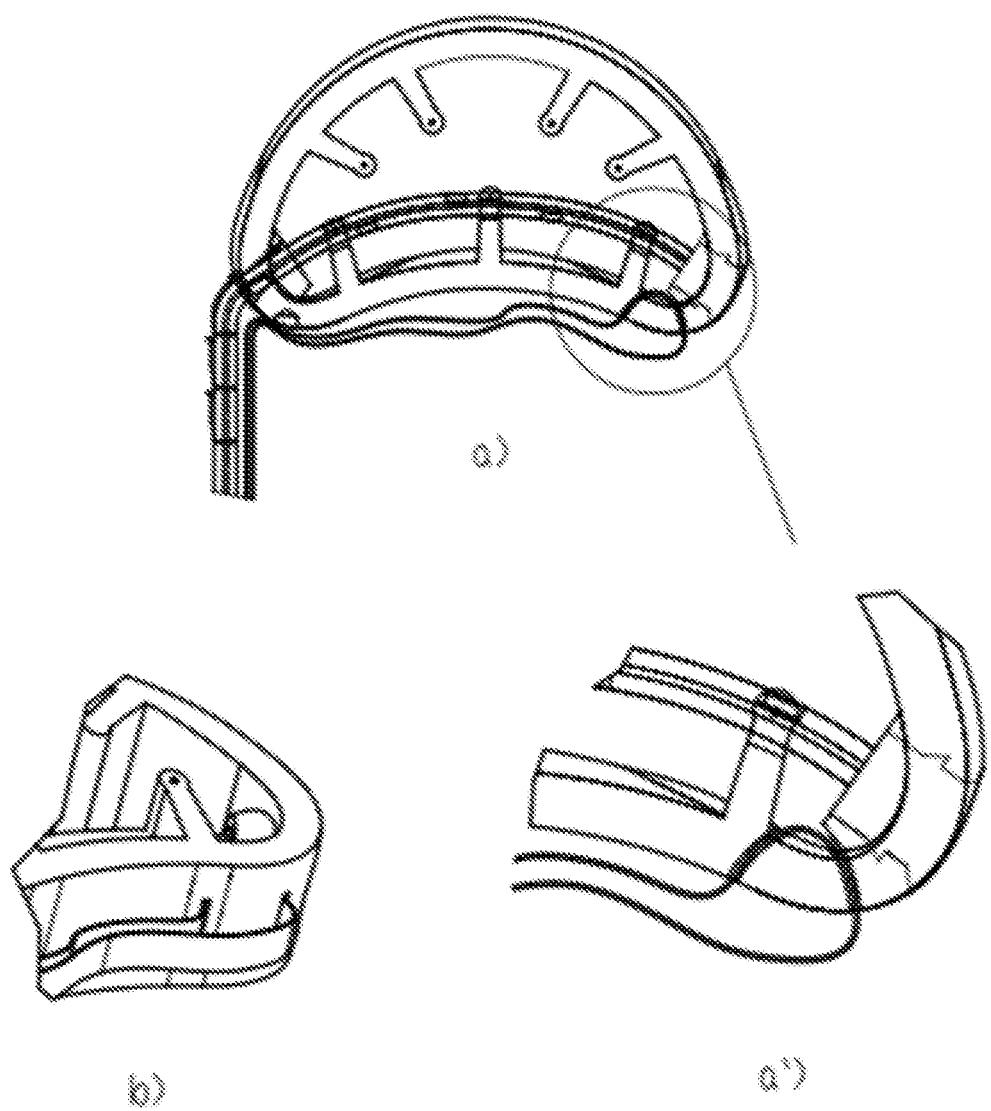
FIG. 6a: Axial view of the semi-rigid ring armed with the closure element and the positioning element.
FIG. 6b: Detail perspective view of the semi-rigid ring, focused on its posterior face and distal pole of the positioning element.

On the posterior face of the distal section of the semi-rigid ring, there are a pair of slots arranged between the most distal support rib and the entry hole of the closure element (FIG. 6). These give way to the positioning strip element that allows to maintain the position of the distal pole, as posterior as possible at the time of the insertion of the device.

Figure 8:
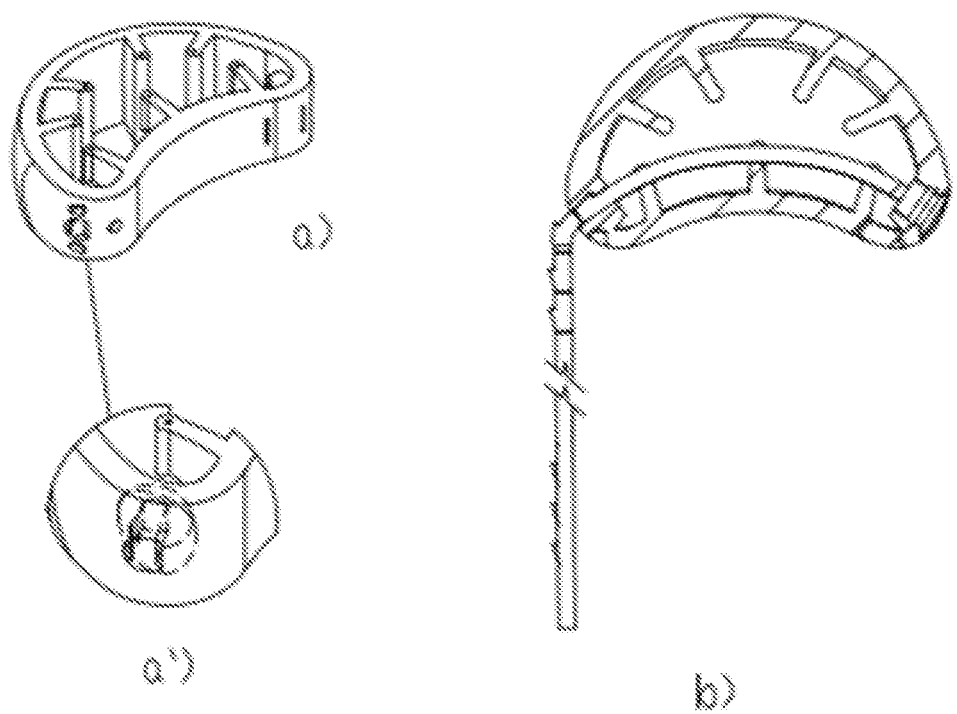
FIG. 8a: Isometric view of the semi-rigid ring, oriented towards the posterior face and proximal pole.
FIG. 8b: Axial section view of the semi-rigid ring indicating the location of the closure element from the inside towards the surgical area.
Figure 12:
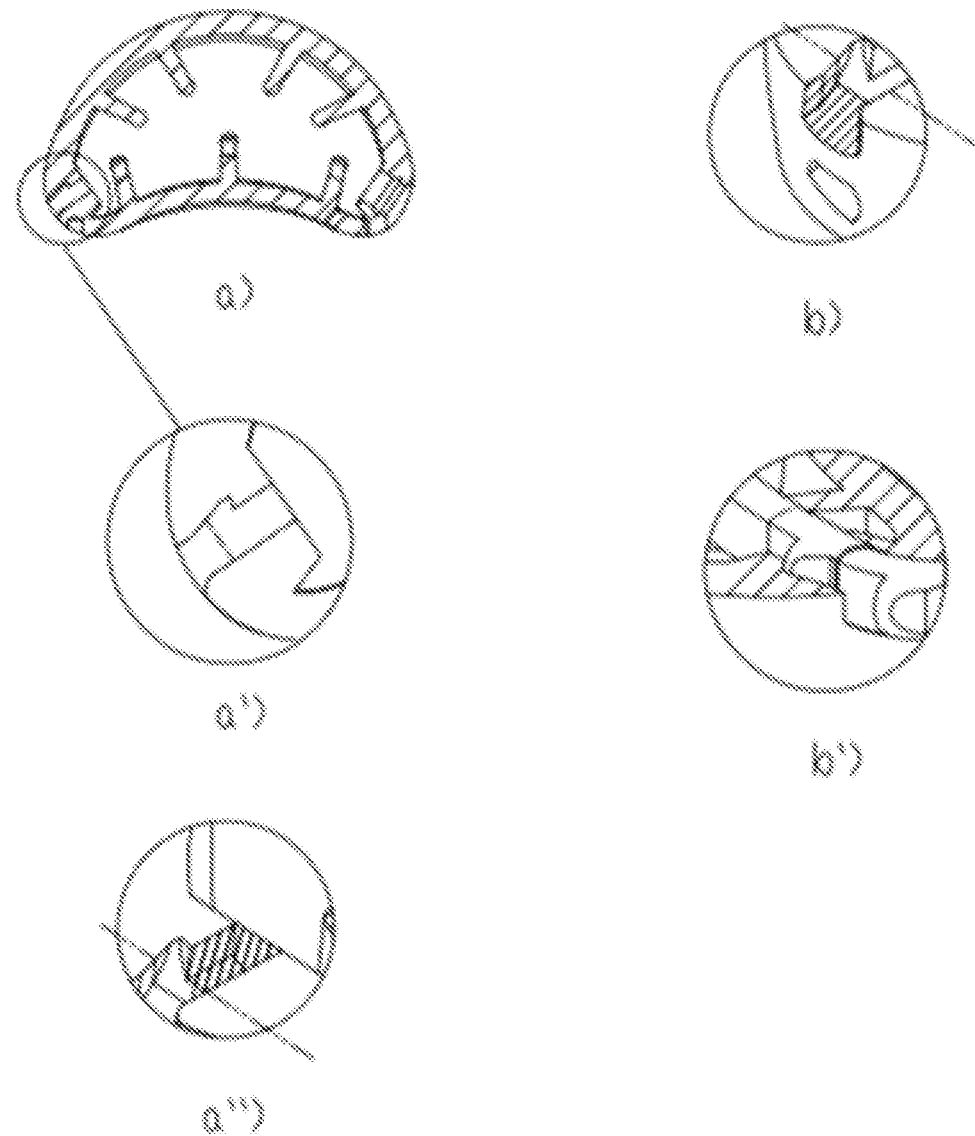
FIG. 12a: Axial section view of the semi-rigid ring.
FIG. 12b: Detail perspective view of the proximal portion of the tubular exit hole, indicating the fastening area of the closure element.
Figure 13:
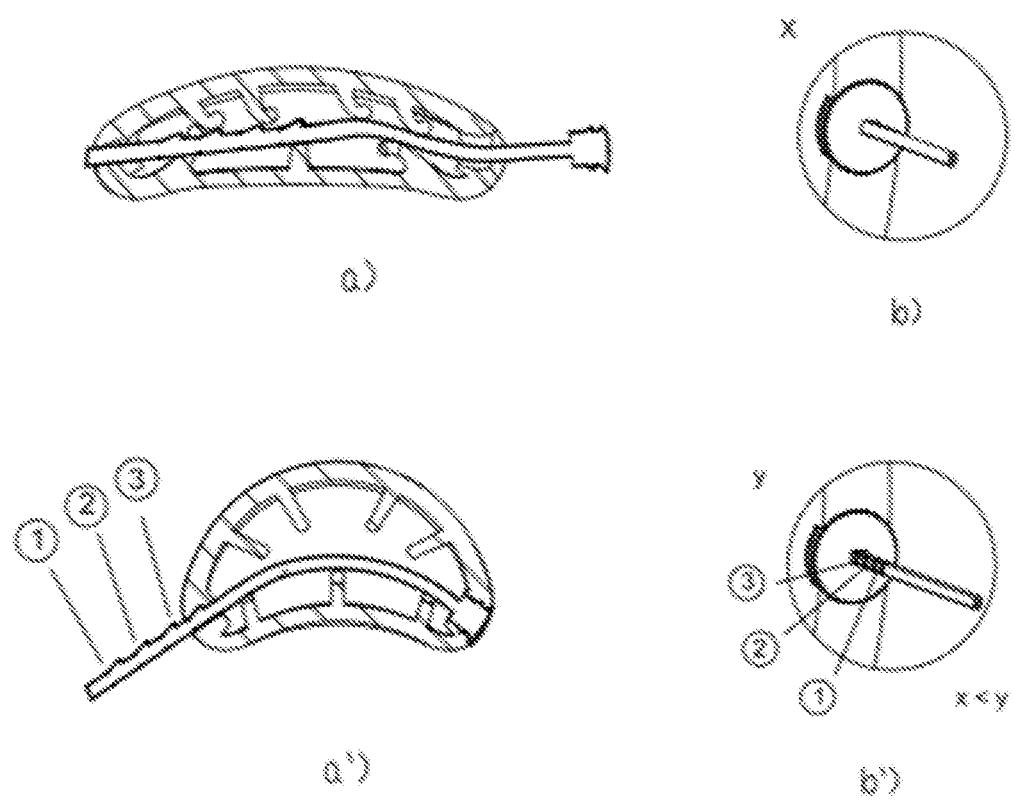
FIG. 13a: Axial section view of the semi-rigid ring in its minimum interior space configuration, while the closure element is being inserted, the projections of the elements are all inside the semi-rigid ring.
FIG. 13b: Detail view of the closure element exiting the removal instruments, when the semi-rigid ring is in its minimum space configuration, the number of projections "x" at the instruments exit is zero.
Figure 14:
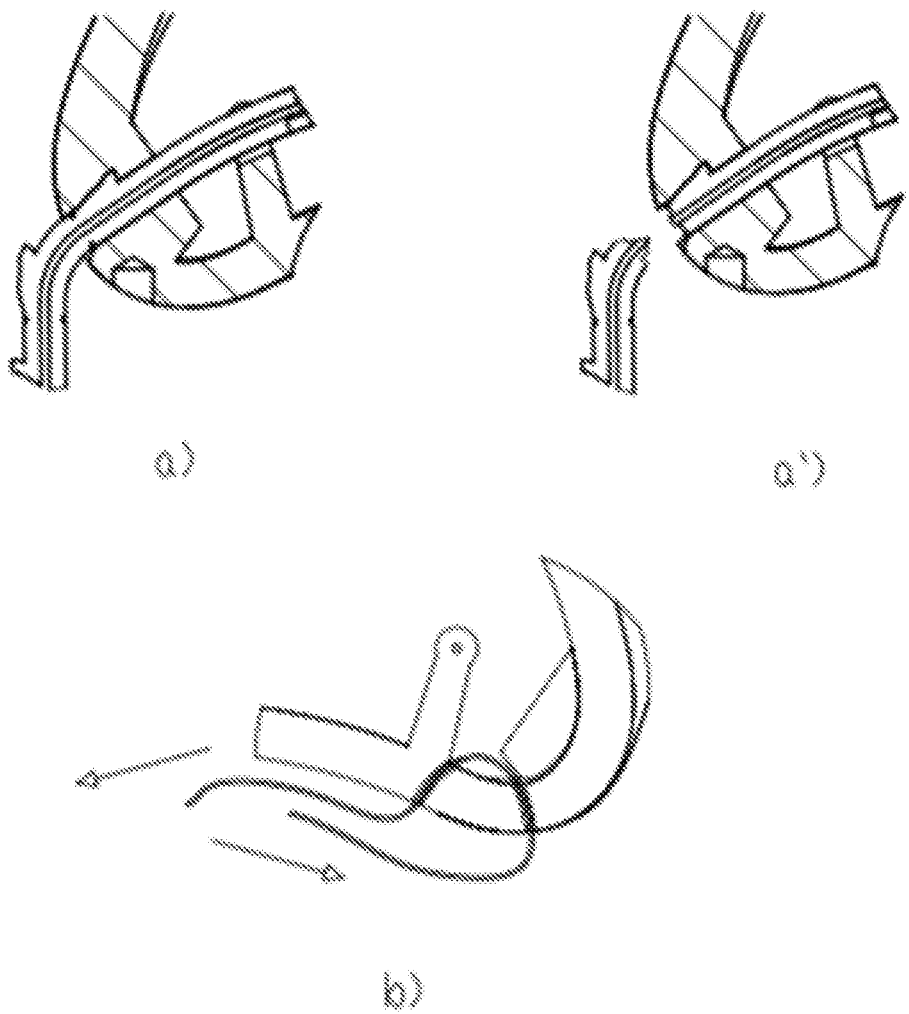
FIG. 14*a*: Axial section view of the proximal pole of the semi-rigid ring next to the closure element in its armed position.
FIG. 14*b*: Axial view of the distal pole of the semi-rigid ring, indication of detachment of the positioning element of the semi-rigid ring, after its location in the disc space.

Proximal Ring Section:

This section corresponds to the area of the device in which the closure element secures the working configuration of the semi-rigid ring. In this segment, the semi-rigid ring is characterized by having a tubular exit hole, whose coronal section represents a cylinder with its front and posterior faces truncated (FIG. 8a, a'). On the anterior face, it has a small recess that serves as a hook to the locking elements of the anterior face of the closure element (FIG. 12a, a', a"). This recess divides the tubular exit hole into a distal or internal portion (FIG. 12a") and a proximal or external portion, with respect to the inside of the semi-rigid ring (FIG. 12b), in which the tolerance of its diameters allows that the rotation of the closure element, around its longitudinal axis, section it without burrs on the surface of the semi-rigid ring (FIG. 14a, a').

Figure 9:
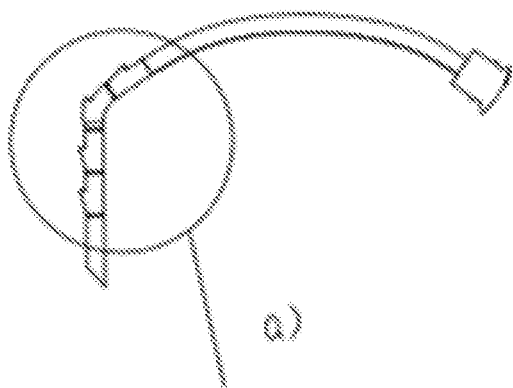
FIG. 9a: Axial view of the closure element from the distal pole to the section with the locking elements in its proximal pole.
FIG. 9b: Perspective view of the semi-rigid ring in axial section, together with its closure element positioned in the proximal pole.
Figure 9:
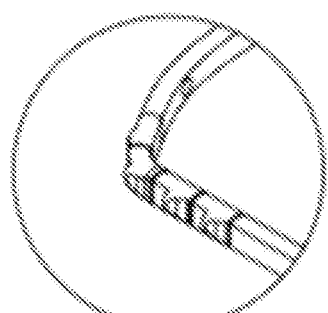
Figure 9:
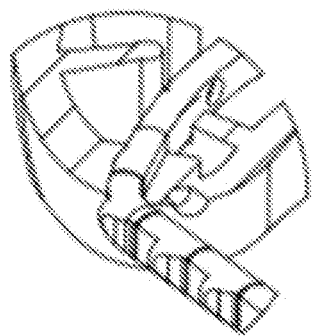
Figure 10:
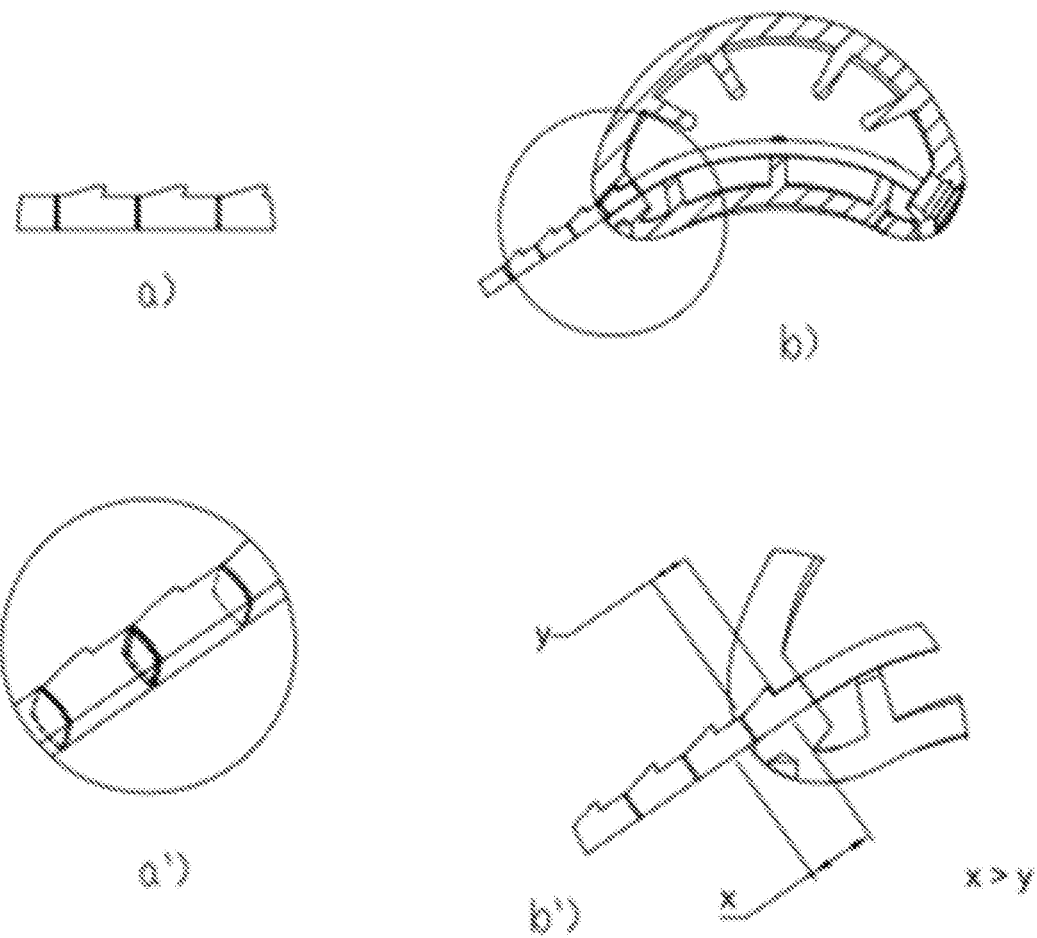
FIG. 10a: Axial view of the proximal pole of the closure element focused on its locking elements.
FIG. 10b: Axial section view of the semi-rigid ring and of the closure element mounted in its working position, from its distal pole to its locking elements.

In this region of the AAD the closure element maintains a cylindrical section with its truncated anterior and posterior surfaces so that it is congruently related to the shape and diameters of the tubular exit hole as described in relation to the securing slots in the posterior support ribs of the semi-rigid ring (FIG. 9; 11c, c'). The congruence of the faces of both parts of the AAD prevents axial rotation of the closure element within the limits of the semi-rigid ring. Once the distal margin of the tubular exit hole is crossed, the closure element can rotate freely, making its rupture possible (FIG. 14a'). This rupture is facilitated and guided by suitable diameter reductions arranged between the locking elements of the closure element (FIG. 10a, a', b).

Figure 29:
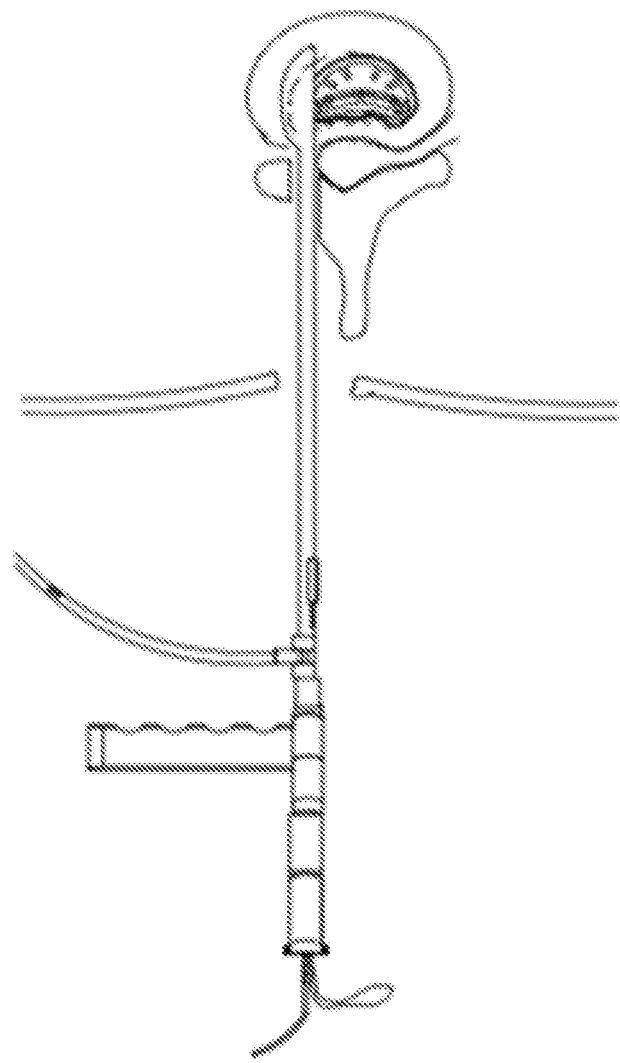
FIG. 29, Axial view of the surgical field.

Extra Annular Section of the AAD:

Once the closure element passes through the exit hole of the semi-rigid ring, it maintains its axial section. In this section, it has no obstacles in a section equivalent to the distance between the exit hole from the semi-rigid ring and the traction element of the device insertion instruments (FIG. 16a"; 17A; 27b). In the most proximal portion of this segment, a new group of locking elements assure the armed instruments of the AAD (FIG. 1d, d"). Finally, the most proximal end of the closure element has a congruent section with a universal "luer lock" adapter, through which it is possible to access its internal conduit for the administration of bioactive materials inside the AAD These penetrate into the semi-rigid ring by means of the perforations described in the intra-annular segment of the closure element. (FIG. 29).

The construction of the AAD considers biocompatible, osteoinductive, and radiologically lucid materials, both with shape memory and stable structure and behavior to human body temperature, although in its synthesis the possibility of mixing them is excluded, as it is the case of some osteoinductive metal inserts at the tips of the posterior ribs or shape memory materials in the structure of the semi-rigid ring itself. The metal inserts allow the positioning of the device under radioscopic guidance while offering an osteoinduction point and a minimum anchorage to further ensure the AAD in its working position.

During its placement, the anterior-posterior axis and the interior area of the AAD are minimized, in order to allow its arrangement inside an insertion cannula, thus allowing its installation with criteria for protection of the spinal canal neural elements.

As previously described, a strip-shaped positioning element made from a low friction coefficient polymer is temporarily attached to the distal pole of the semi-rigid ring, in the manner of reins, through the two slots located on the posterior face of this section of the semi-rigid ring.

This structure leads the closure element into the insertion instruments, exceeding it by a sufficient length to ensure, by means of its traction, the position of the most distal pole of the AAD at the time of installation. Once the correct position of the device is confirmed, said closure element is removed by simply pulling one of its ends.

Surgical Technique

Insertion of the AAD

The posterior approaches are, by far, the most used for accessing the dorsal aspect of the intervertebral disc in the lumbosacral region. These types of techniques conventionally require a deep dissection and a considerable area of removal of the erector spinae muscles and some intervertebral ligaments. At present, there is consensus regarding the parallelism between the damage inflicted on this musculature and other soft parts and the evolution of postoperative pain and compromise of the stability of the affected spinal unit.

In the last decades, with the purpose of minimizing the damage on the musculoskeletal behavior by means of the separation of fibers and not the removal of the same, a considerable number of approach systems have been developed that make it possible to install in the surgical field a cannulated work path of small diameter without removing muscle fibers during its installation. This is the case, for example, of the METRx system developed by Sofamor-Danek.

Tubular approach systems, such as the previously mentioned, allow for the stable protection of a small diameter work cylinder, exactly above the level of the spinal lesion to be treated. By this, a minimum mechanical and thermal impact on the soft tissues is ensured and, therefore, a scenario of less pain and shortening of the postoperative period is possible.

The instruments described below that allow the implantation of the AAD have a conception similar to that previously mentioned and can be used both for standard microsurgical approach routes and for those necessary for the removal of a nucleus pulposus lesion with an endo- or exoscopic microsurgical criterion.

The material has been divided, for its description, in relation to the procedures of insertion, assembly and eventual removal.

Insertion Instrumental

Figure 30:
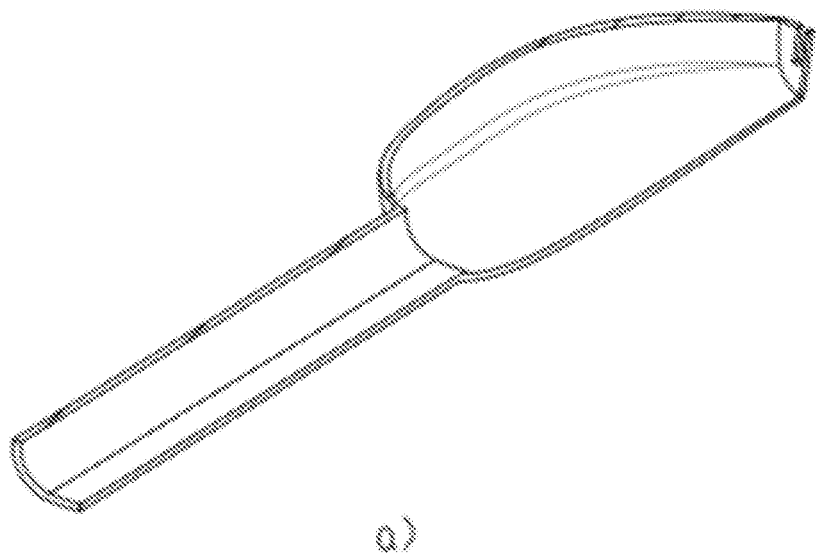
FIG. 30a: Axial perspective view of the distal portion of the insertion cannula of the insertion instruments, of hemi-ovoid distal shape.
Figure 30:
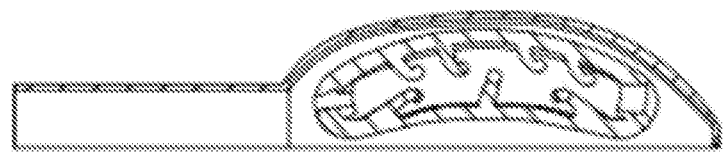
Figure 31:
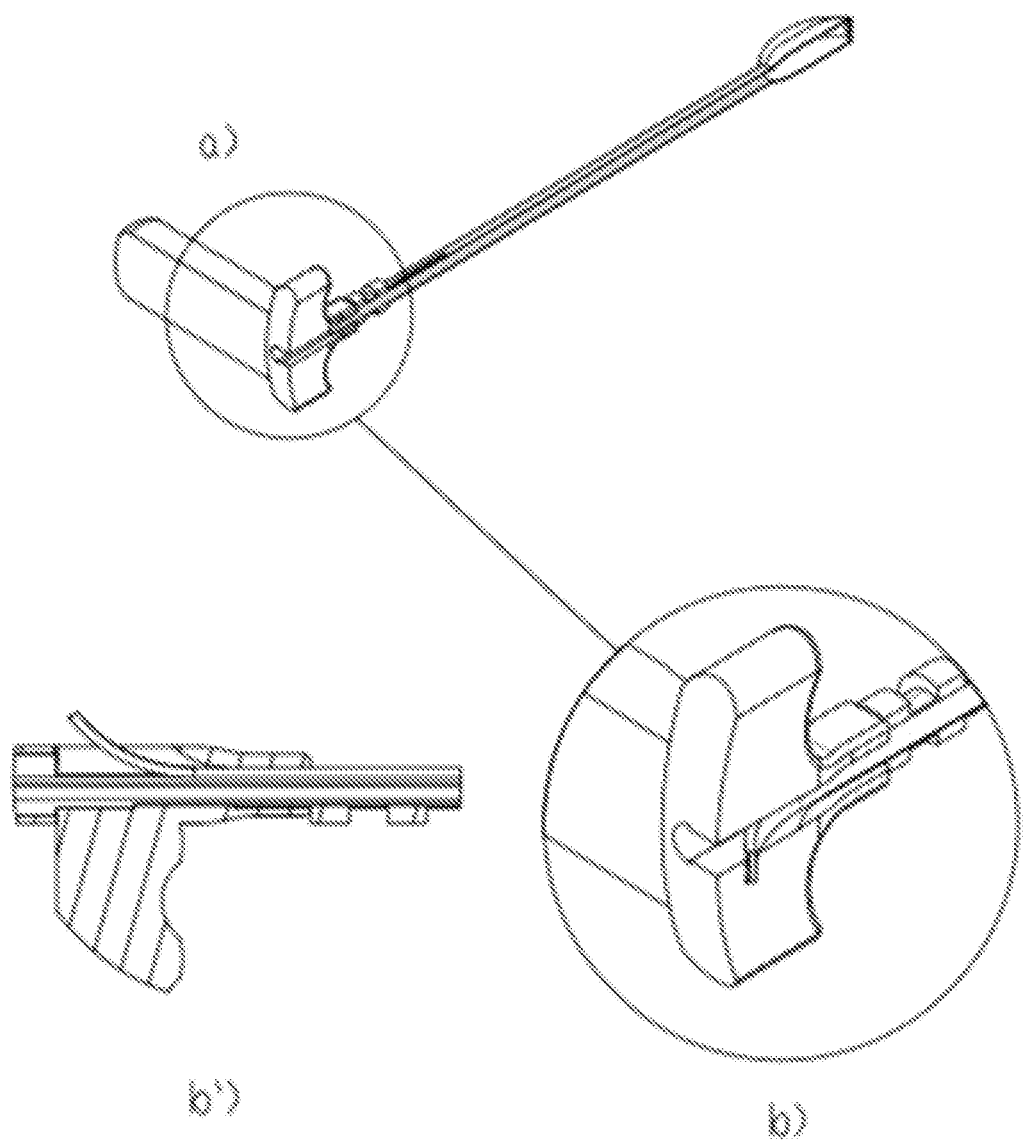
FIG. 31a: Isometric view of the insertion cannula of the insertion instruments.
FIG. 31b: Detail view of the proximal portion of the insertion cannula, focused on the T-handle.
Figure 32:
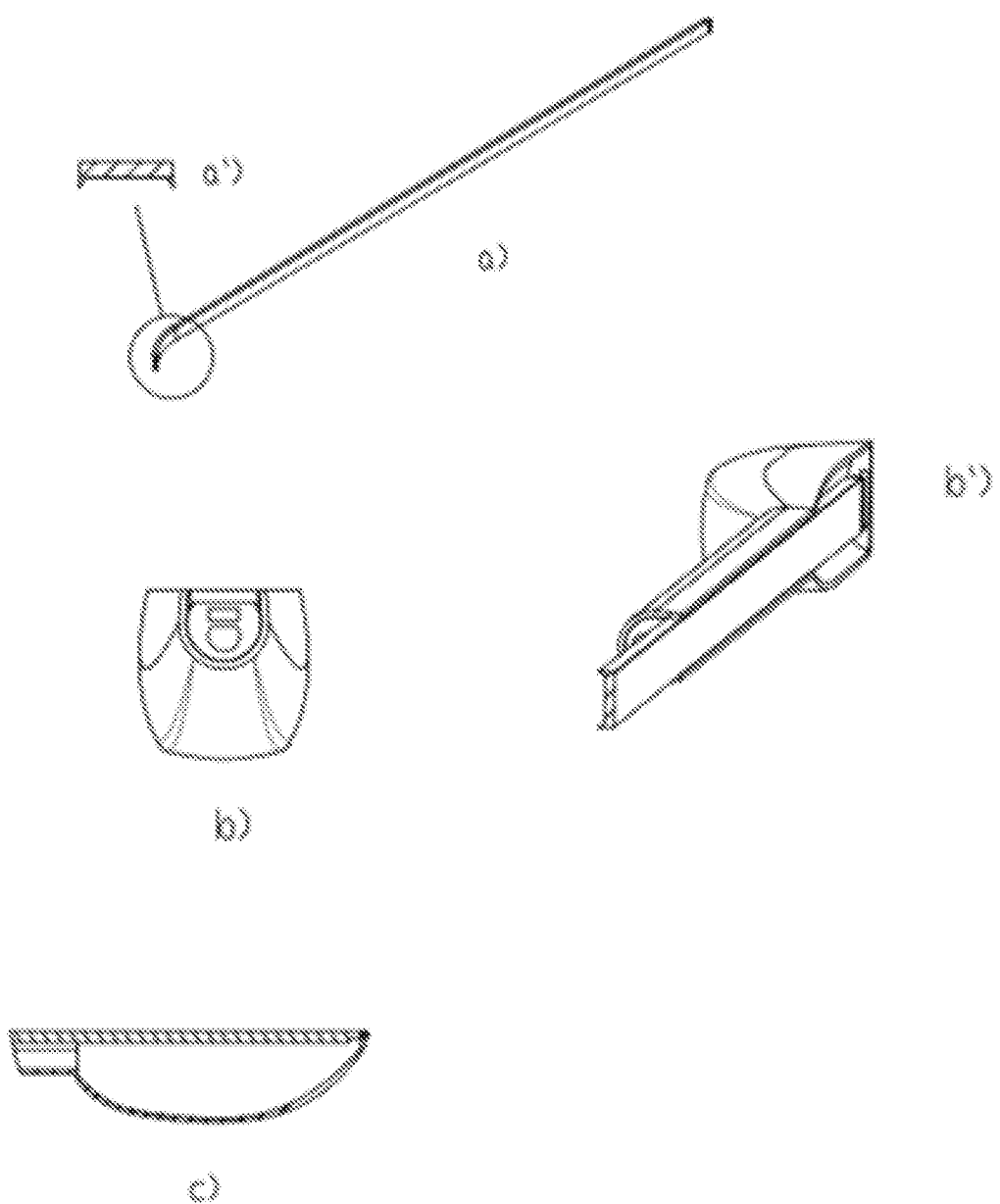
FIG. 32a: Isometric view of the closure sheet of the insertion instruments.
FIG. 32b: Detail view of the distal portion of the assembly formed by insertion and pushing cannulas, and closure sheet in sagittal section.
FIG. 32c: Axial section view of the insertion cannula and the closure sheet in the distal portion, where the sheet is closed to prevent its displacement.

In this group the following instruments are considered:

1. Insertion Cannula: It is a tubular section structure having a tip with a hollow and hemi-ovoid shape in which the AAD is encapsulated in its entry position to the disc (FIG. 30), a cylindrical middle portion, and a proximal handle. This tool has a sufficient length for comfortable handling from outside the surgical field. Throughout the length of its medial face, with respect to the patient's middle sagittal plane, it has a slot. In this slot a closure sheet of the distal and middle portion of the cannula is inserted (FIG. 32b, b', c). In its proximal portion, this cannula also has a T-handle arranged with its axis perpendicular to the longitudinal axis of the cannula, having a concave face towards the medial that optimizes the operator's vision towards the surgical field (FIG. 31b, b'). Two diameter increases of the cannula immediately adjacent to the handle, define an anchor point for a self-static fixation system to the surgical table and for the operation of a hammer with diapason, which allows the insertion and removal of the cannula in the intervertebral space (FIG. 31b). A snap located on the medial face of the proximal region of the middle tubular section of the instrument, allows for the securing of the closure sheet and the locking of movement of the pushing cannula arranged therein (FIG. 29; 33).

Figure 22:
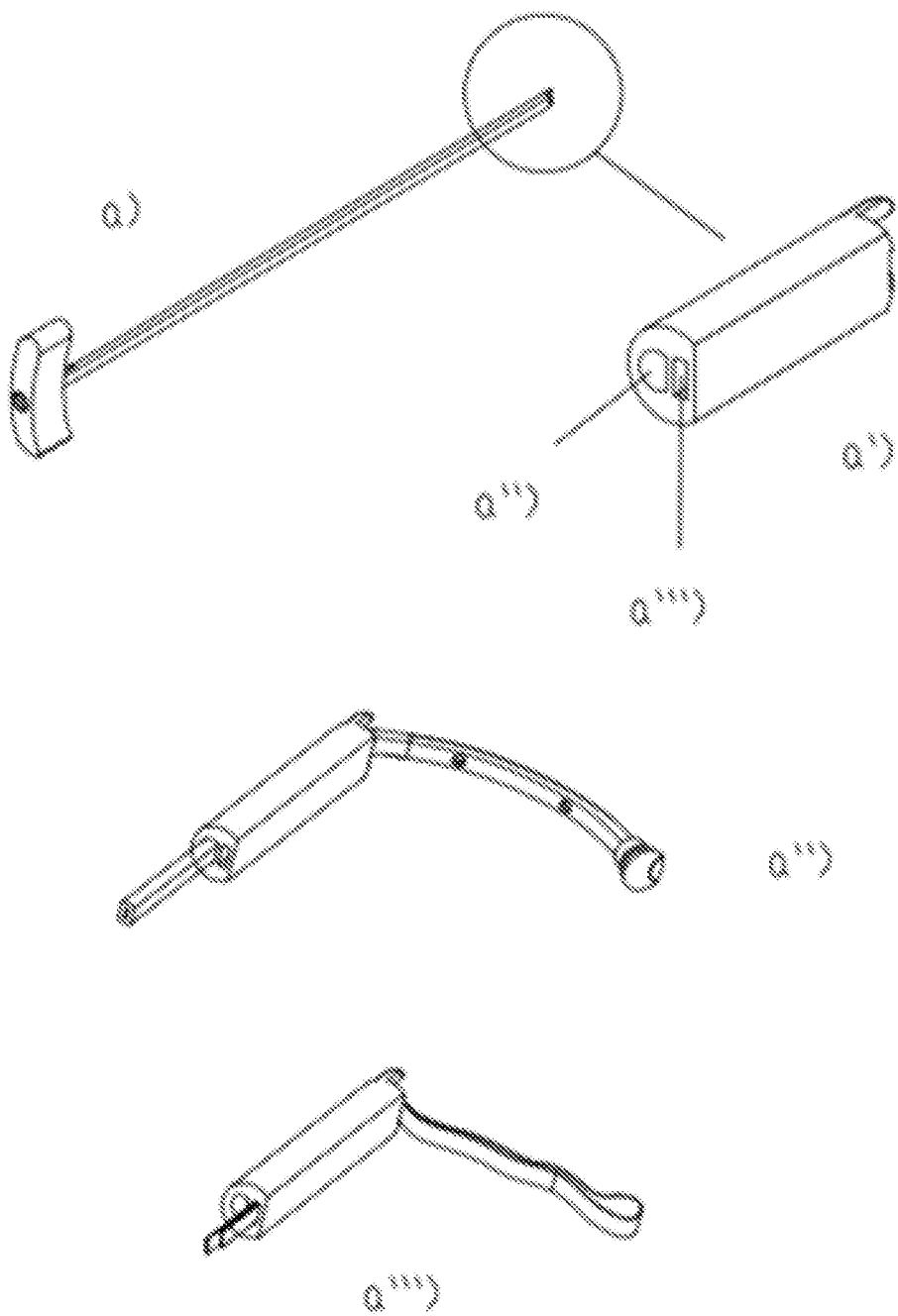
FIG. 22*a*: Isometric view of the pushing cannula of the insertion instruments.
Figure 23:
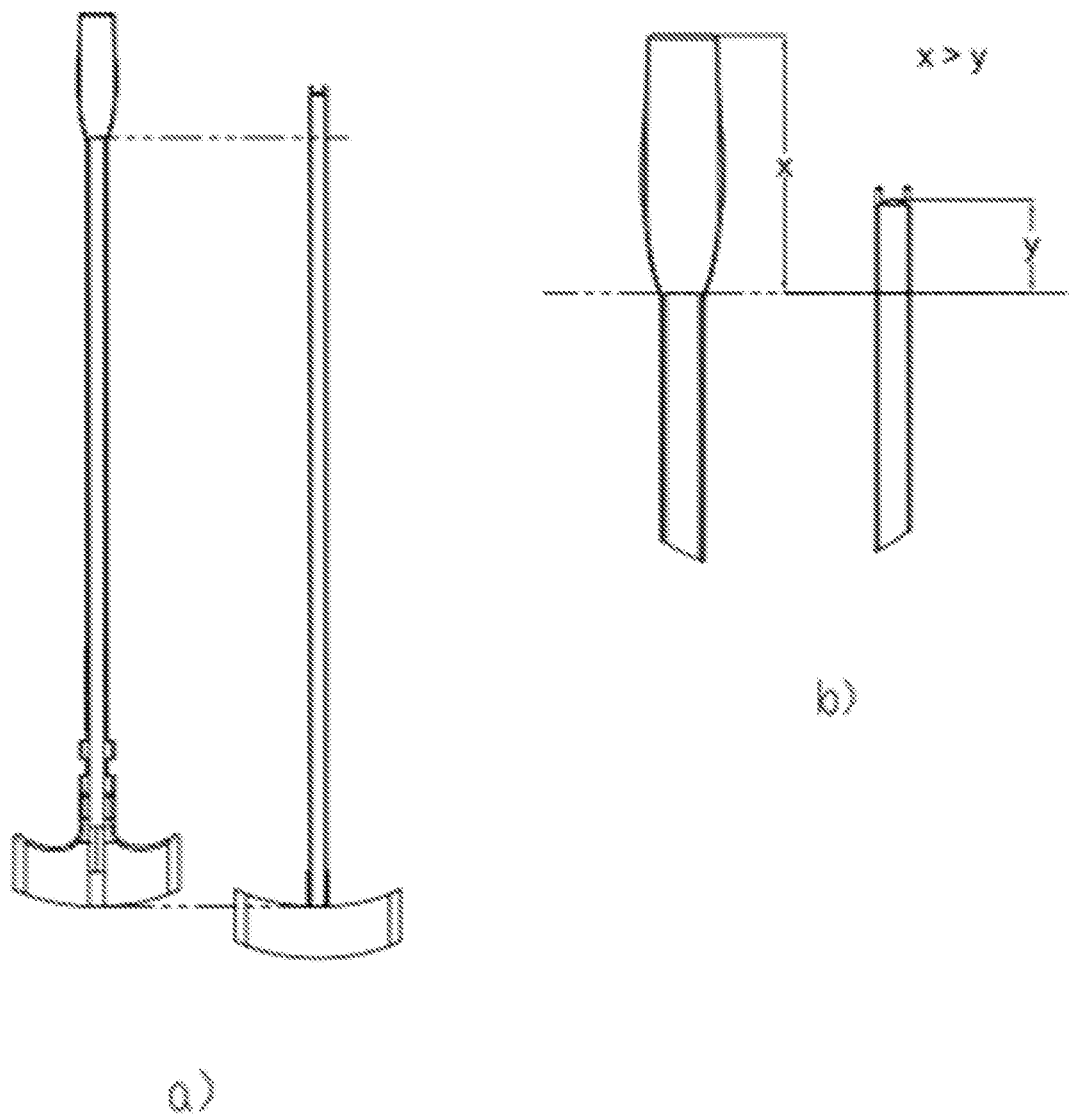
FIG. 23*a*: Sagittal view of the pushing cannula and the insertion cannula of the insertion instruments, comparison of lengths from the most distal pole of the handle of the pushing cannula.
FIG. 23*b*: Detail view of the distal poles of the pushing cannula and the insertion cannula, the comparison of length under the same reference, the distance to the distal pole of the pushing cannula "y", is less than the distance to distal pole of the insertion cannula "x"
Figure 24:
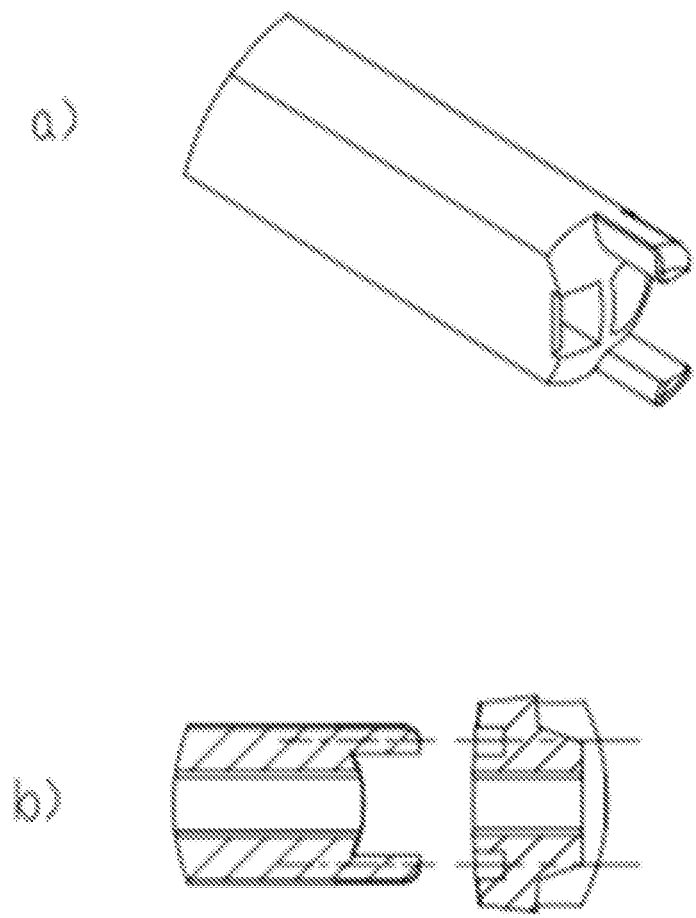
FIG. 24*a*: Detail view of the distal pole of the pushing cannula of the insertion instrument, in perspective towards the distal pole, focused on the connecting protuberances.
FIG. 24*b*: Sagittal section view of the pushing cannula of the insertion instruments and cross section of the semi-rigid ring in the posterior proximal pole, where the anchoring holes are located, line of action where both pieces match.
Figure 25:
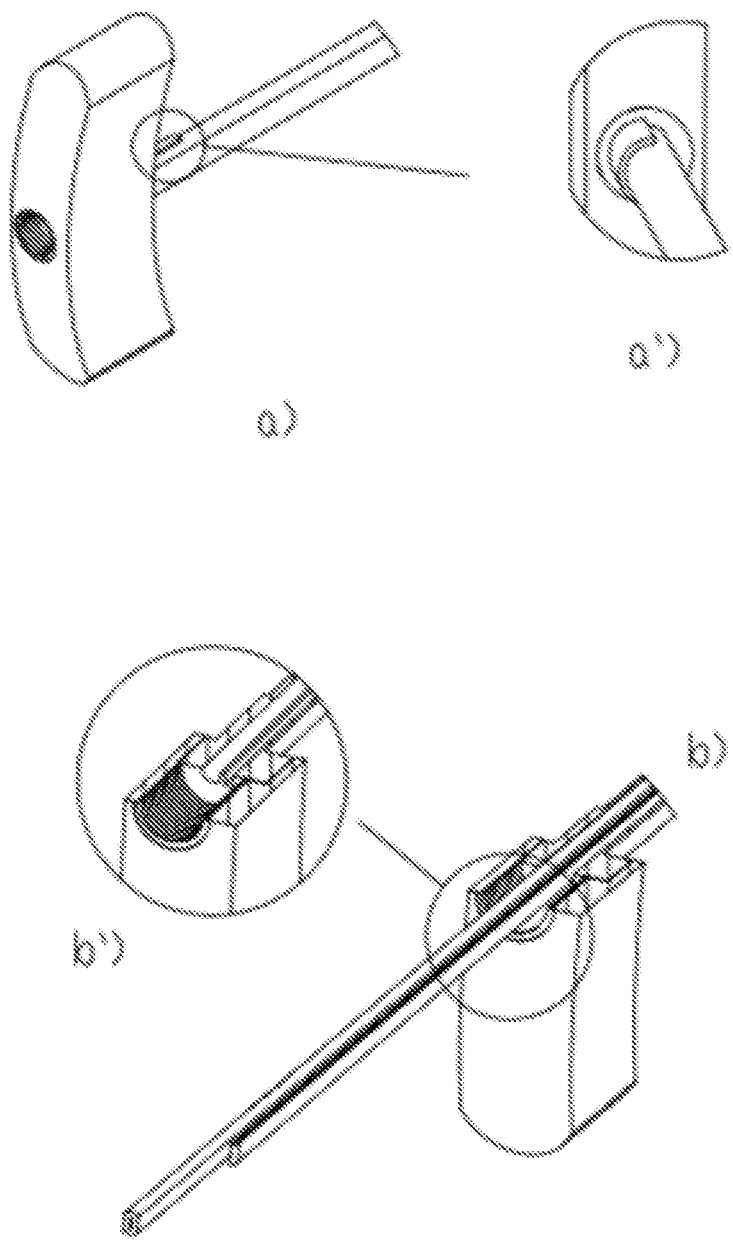
FIG. 25*a*: Detail view of the proximal pole of the pushing cannula of the insertion instruments, focused on the cannula handle.
FIG. 25*b*: Axial section view, in perspective, of the distal pole of the pushing cannula of the insertion instruments, the closure element and the positioning element pass through the handle through the threaded hole.
Figure 33:
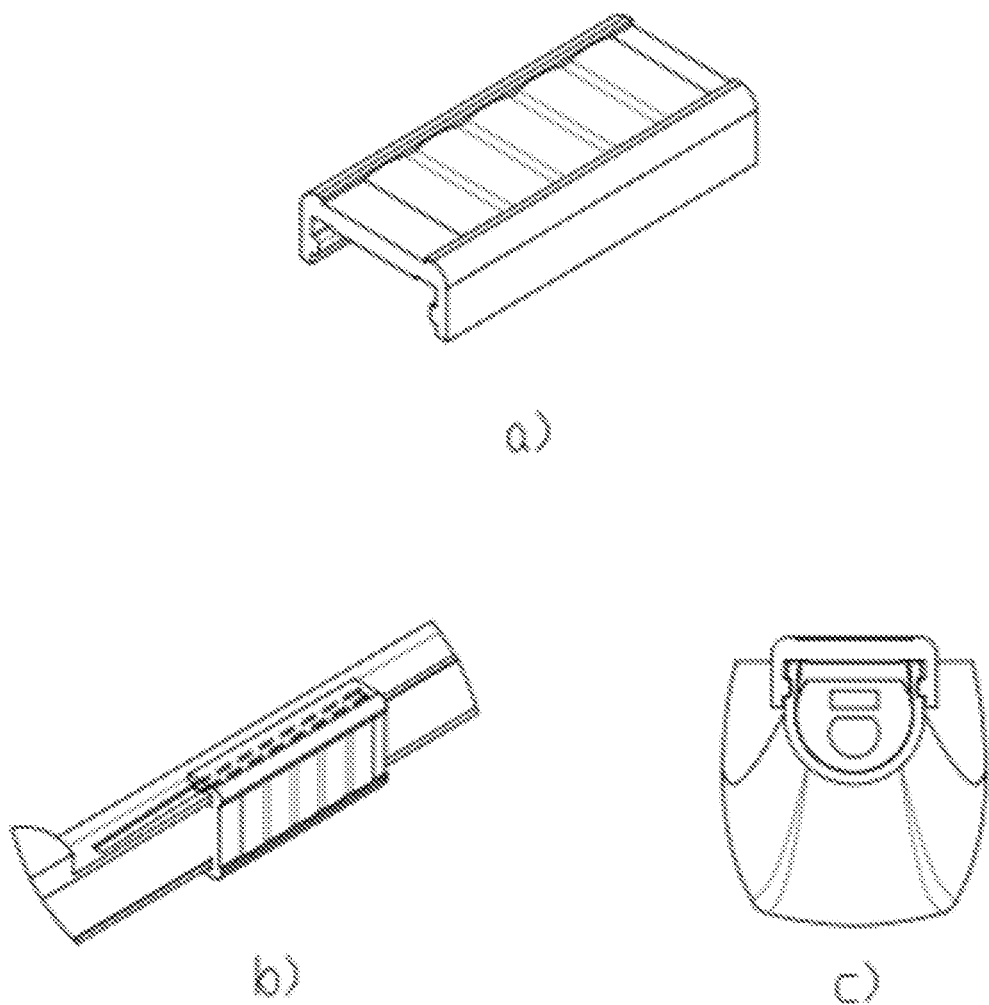
FIG. 33a: Isometric view of the insertion tool snap.
FIG. 33b: Perspective view of the housing of the closure sheet locking, in the proximal portion of the insertion cannula.
FIG. 33c: Sagittal section view of the insertion cannula set, pushing cannula, closure sheet and snap.
Figure 34:
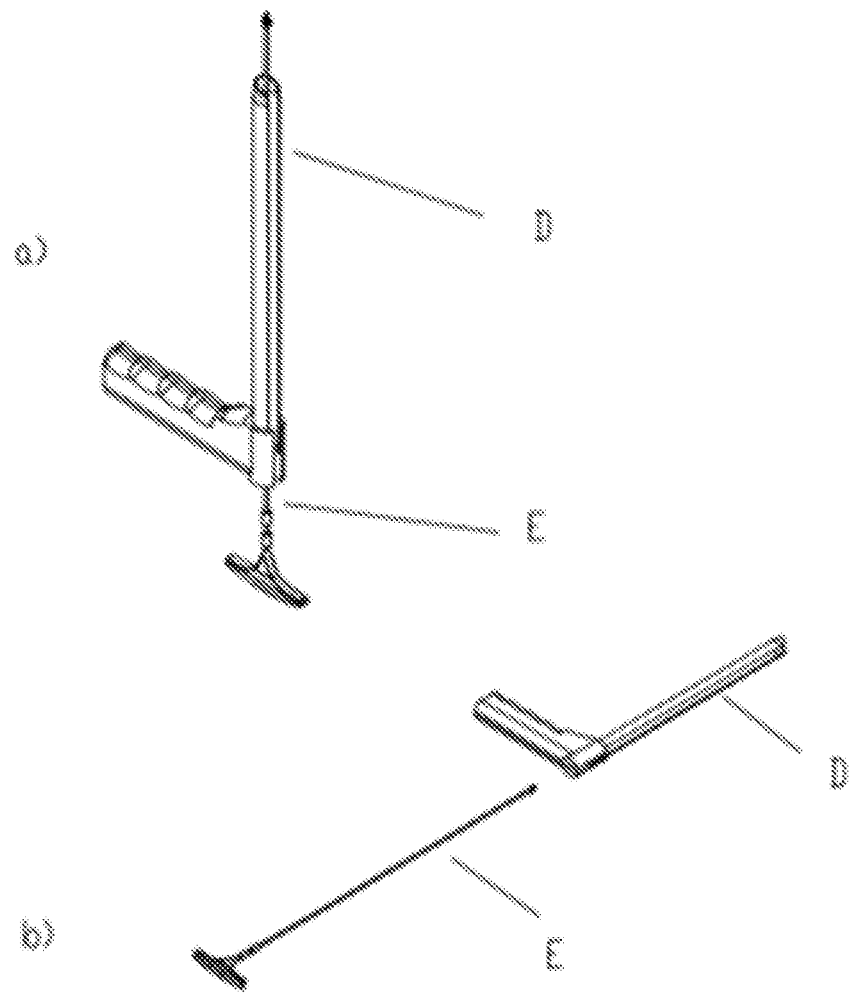
FIG. 34a: Isometric view of the removal instruments, assembled in working position, consisting of, extraction cannula (D), extraction rod (E)
FIG. 34b: Isometric view of removal instruments, not assembled.

2. Pushing cannula: This instrument made from plastic or non-ferrous metal, with an equally cylindrical section, has a certain diameter and congruence that allows for its insertion, and longitudinal and rotational displacement in the core of the insertion cannula (FIG. 33c; 28b, b", b"). Its length does not exceed the length of the insertion cannula (FIG. 23). In its distal pole, this instrument has two protuberances that coincide with the perforations that the semi-rigid ring of the AAD has in the proximal pole just in front of the exit hole that the semi-rigid ring has for the closure element. (FIG. 15a, a'; 24). These perforations define a competent anchor that ensures adequate pressure of the device at the time of its insertion. The working section of this cannula defines a cylinder with its medial face truncated, with two eccentric perforations (FIG. 22a', a", a'''). A lateral perforation that allows for the passage of the closure element of the AAD (FIG. 22a") and a medial perforation that allows for the passage of the positioning element of the distal pole of the AAD (FIG. 22a'''). The perforations have axial sections with suitable, shapes, diameters and tolerances to facilitate the passage of the described elements. In its proximal pole, this instrument has a handle with medial concavity that in the medial axis presents a widening, with its walls conveniently threaded for the accommodation of the locking and securing screw of the AAD (FIG. 25*a*, *b'*). Immediately distal to this handle, the tubular portion of the instrument has, on its lateral face, an increase in diameter that allows it to be assembled with the insertion cannula. (FIG. 25*a*, *a'*).

Instrumental Assembly of the AAD

Figure 26:
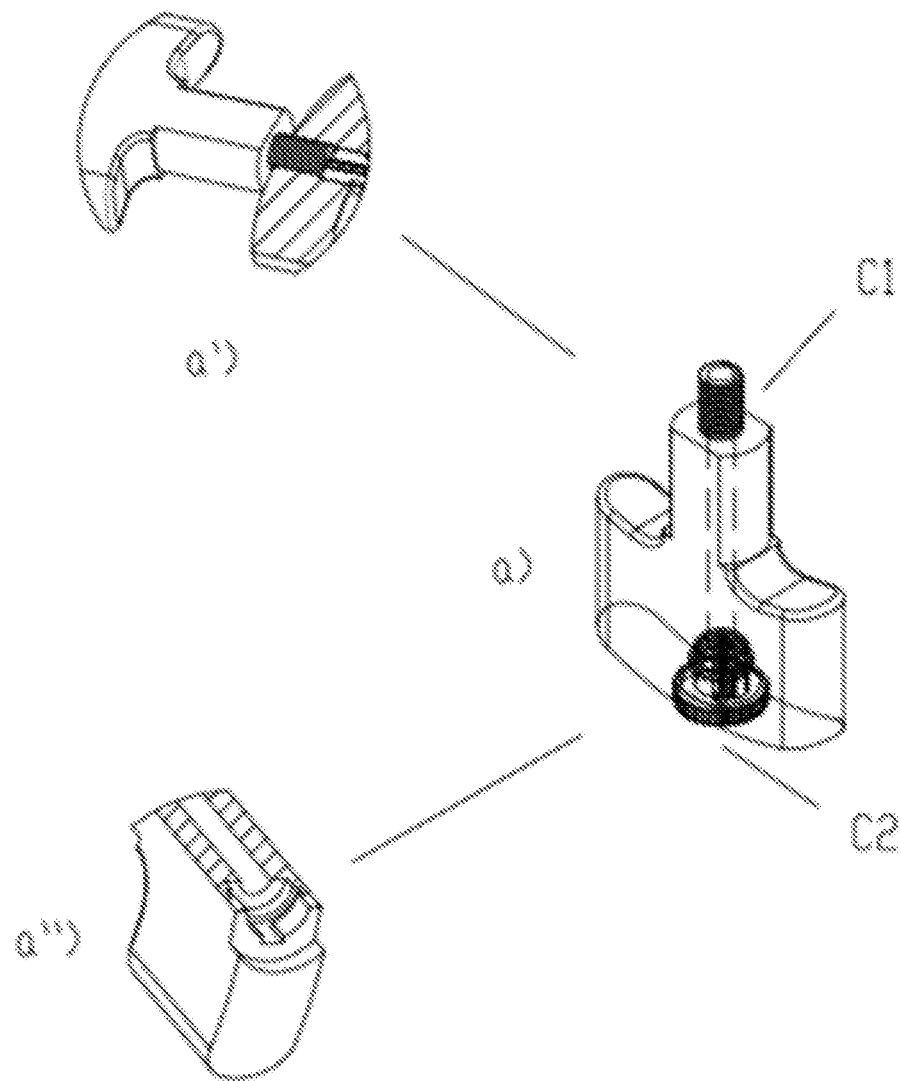
FIG. 26*a*: Isometric view of the assembly instruments, composed of a locking screw (C1) and a twisting lock (C2), a hollow canal can be seen in the locking screw from the distal pole to the proximal tubular portion, where the twisting lock is positioned.
Figure 27:
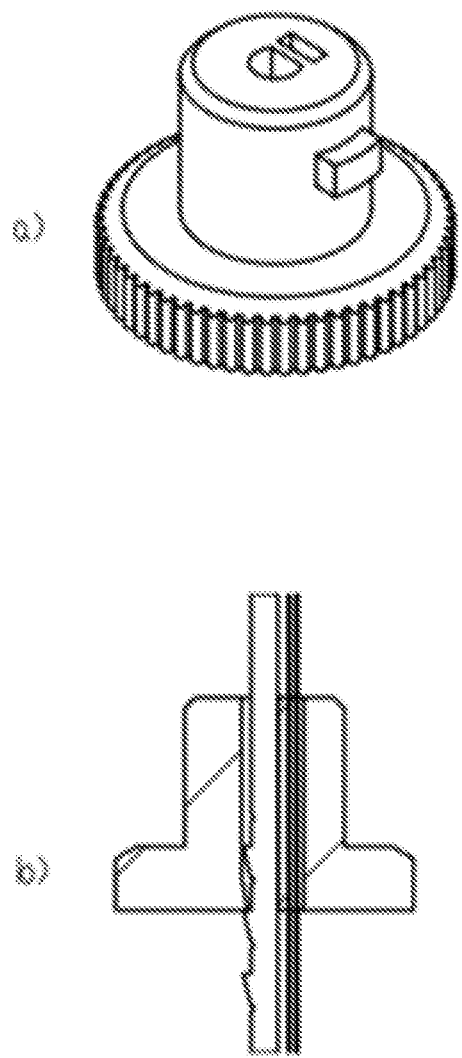
FIG. 27*a*: Isometric view of the twisting lock of assembly instruments.
FIG. 27*b*: Axial sectional view of the twisting lock, indicating the canals for the closure element and the positioning element, in the most proximal pole the canal of the closure element reduces its diameter to generate tension in the same.
Figure 28:
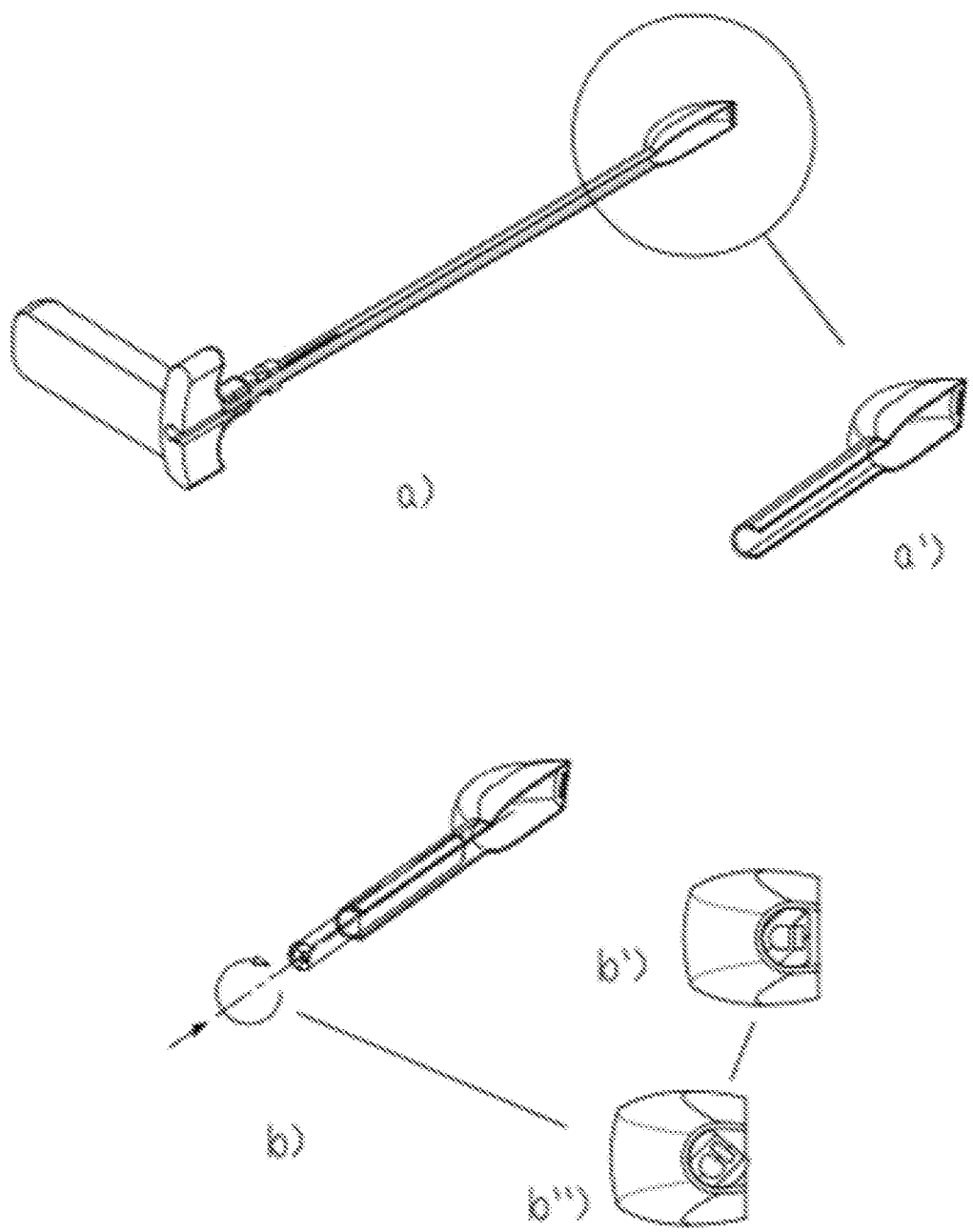
FIG. 28*a*: Isometric view of the insertion cannula of the insertion instruments.
FIG. 28*b*: Detail view of the distal portion of the insertion cannula housing the distal portion of the pushing cannula, the lines indicate the ability of the pushing cannula to rotate and move linearly within its interior.

This group includes the following elements:

1. Locking Screw: This screw preserves the geometry of the handles of the insertion and pushing cannulas with a male pole that is screwed in the increase in diameter described on the handle of the pushing cannula (FIG. 26). Its design foresees that the thread passage of this screw be equivalent to a stable advance of the locking elements of the closure element at the time of unscrewing the locking screw (FIGS. 26*a'* and 27*b*). In its core, the piece is perforated and in its proximal pole this perforation has an increase in diameter that allows for the assembly of a piece with a twisting function (FIG. 26*a*, *a"*). The diameters of the central perforation allow for free passage to both the closure element and the positioning element of the AAD 2. Twisting lock: This piece has a cylindrical portion that is secured with freedom of rotation in the increase in diameter of the proximal face of the locking screw (FIG. 26*a*, *a"*; 27*a*). In its longitudinal axis it has two perforations with the same configuration as in the pushing cannula of the AAD (FIG. 27*a*). At the most proximal point of the perforation, which gives way to the closure element, this piece has a diameter reduction that defines a unidirectional closure for the locking elements that the closure element presents at that height (FIG. 27*b*).

For the assembly of the AAD, the closure element must pass through the locking screw, being fully screwed in the dilation that the pushing cannula conveniently has in its proximal portion, and its proximal portion inserted in the perforations of the proximal pole of the semi-rigid ring. In this position, the pushing cannula is housed inside the insertion cannula and the AAD is secured inside the distal capsule of this instrument.

The assembly lock element secures the closure element against the locking screw.

The insertion cannula is inserted into the disc space throughout its distal dilation. At this time, the diameter of said capsule subtly separates the adjacent vertebrae. The lateral closure sheet of the insertion cannula is retracted proximally, and the pushing cannula is moved forward under intraoperative radioscopic control. This maneuver is parallel to the traction of the traction element of the distal pole of the AAD Once arranged in its correct position, the locking screw is unscrewed against the twisting lock, thus pulling the entire length of the closure element. As this traction progresses, the locks that the closure element has in relation to the proximal hole of the semi-rigid ring preserve the geometry of the ring by approaching its poles. This advance is corroborated by the appearance of marks on the closure element proximal to the twisting lock.

Once the final progression mark is verified, it is possible to remove the positioning strip element by pulling one of its ends. The technique progresses to the filling procedure inside the AAD, which can take place by connecting the closure element to a standard syringe by an ad-hoc means.

Finally, the rotation of the pushing cannula inside the insertion cannula causes the section of the closure element, just as it exits from the inside the semi-rigid ring. The pushing cannula is removed with the assembly instruments and the insertion cannula is finally removed, taking its portion proximal to medial and consequently moving its distal third away from the AAD already armed.

Removal Instrumental

In the current state of art of spinal reconstruction techniques, there are no systems that allow the simple removal of intersomatic implants already arranged in their final working position. Currently, the removal of fusion systems or a prosthetic disc that progresses with problems requires a large retroperitoneal access surgery.

The proposed system, unlike the above-mentioned, allows for the easy extraction of the AAD by means of the following instruments.

Figure 20:
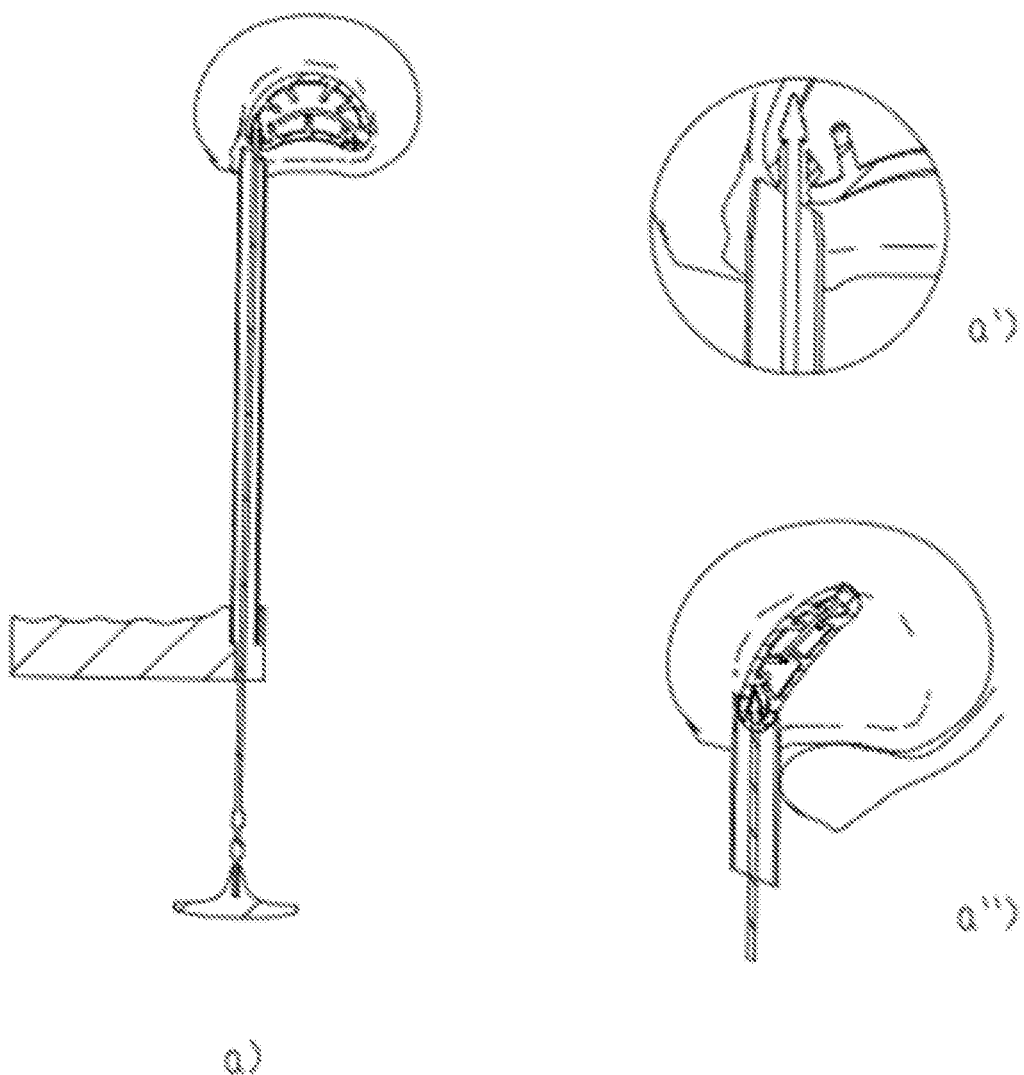
FIG. 20*a*: Axial section view of the extraction cannula, positioned inside the disc space and the extraction rod inside the semi-rigid ring after cutting the closure system.
Figure 21:
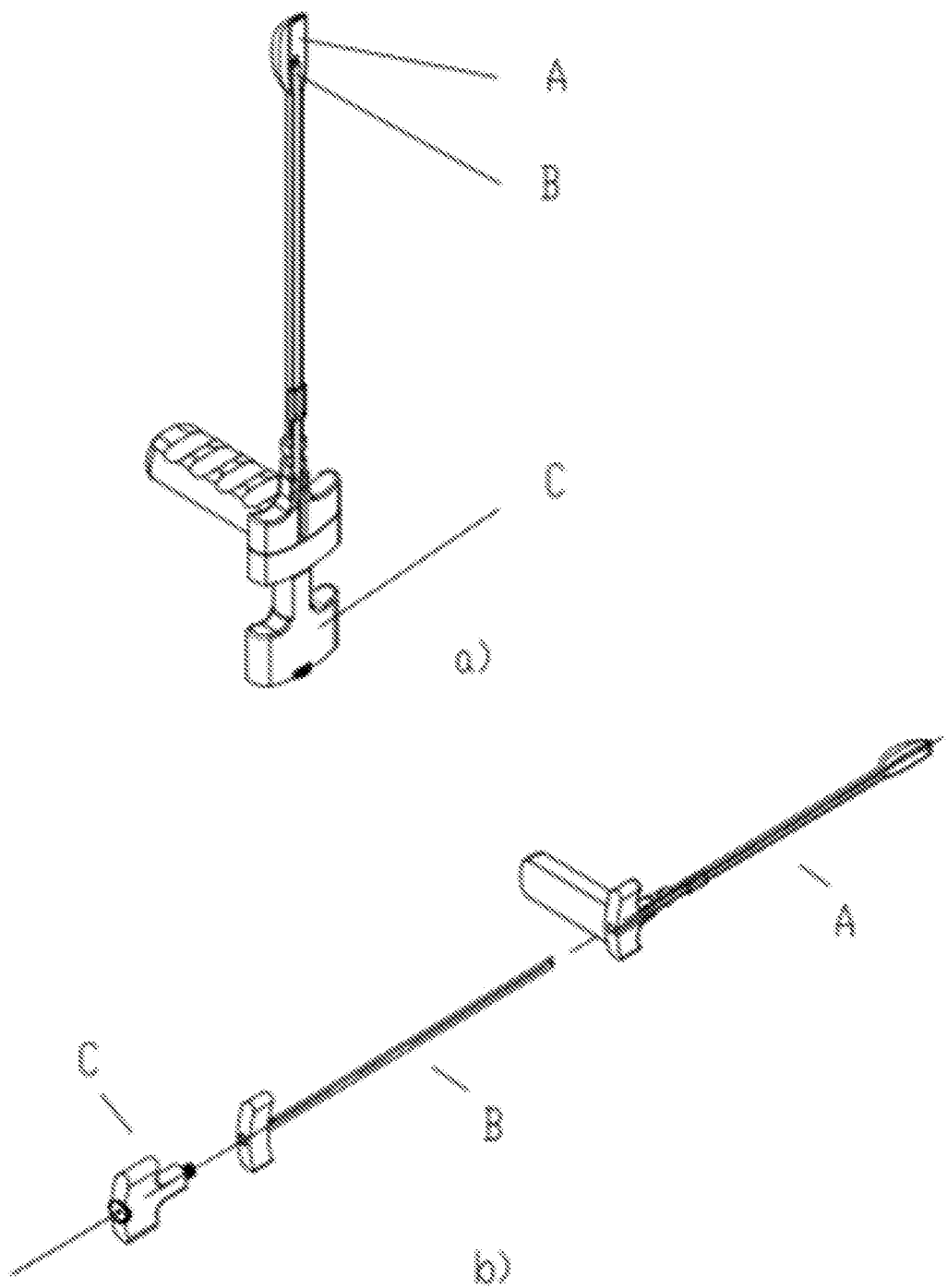
FIG. 21*a*: Isometric view of the insertion instruments, assembled in working position, consisting of insertion cannula (A), pushing cannula (B) and assembly instrument (C)
FIG. 21*b*: Isometric view of insertion instruments, disassembled.

1. Extraction rod: Corresponds to a cylindrical piece of metallic material with a conical and striated tip, having in its base small spikes to ensure its hook in the hole that the semi-rigid ring of the AAD has on the posterior face of the proximal pole (FIG. 36*a*, *a'*). At its opposite end, this rod has a handle. Immediately distal to the handle, two increases in diameter allow the operation of a hammer with diapason to promote the removal of the tool (FIG. 37*a*, *b*). Once the device is identified in the surgical field, the conical and striated portion is inserted through the ad-hoc hole of the posterior face of the proximal pole of the semi-rigid ring (FIG. 36*b*, *b'*). When advancing through the structure of the closure system, the expansion of the conical and striated tip of the extraction rod breaks the closure system and, consequently, disassembles the AAD When crossing its wall, the conical tip of the instrument, acts as an arrowhead capturing the annular assistance device (FIG. 20 *a'*, *a"*).

Figure 35:
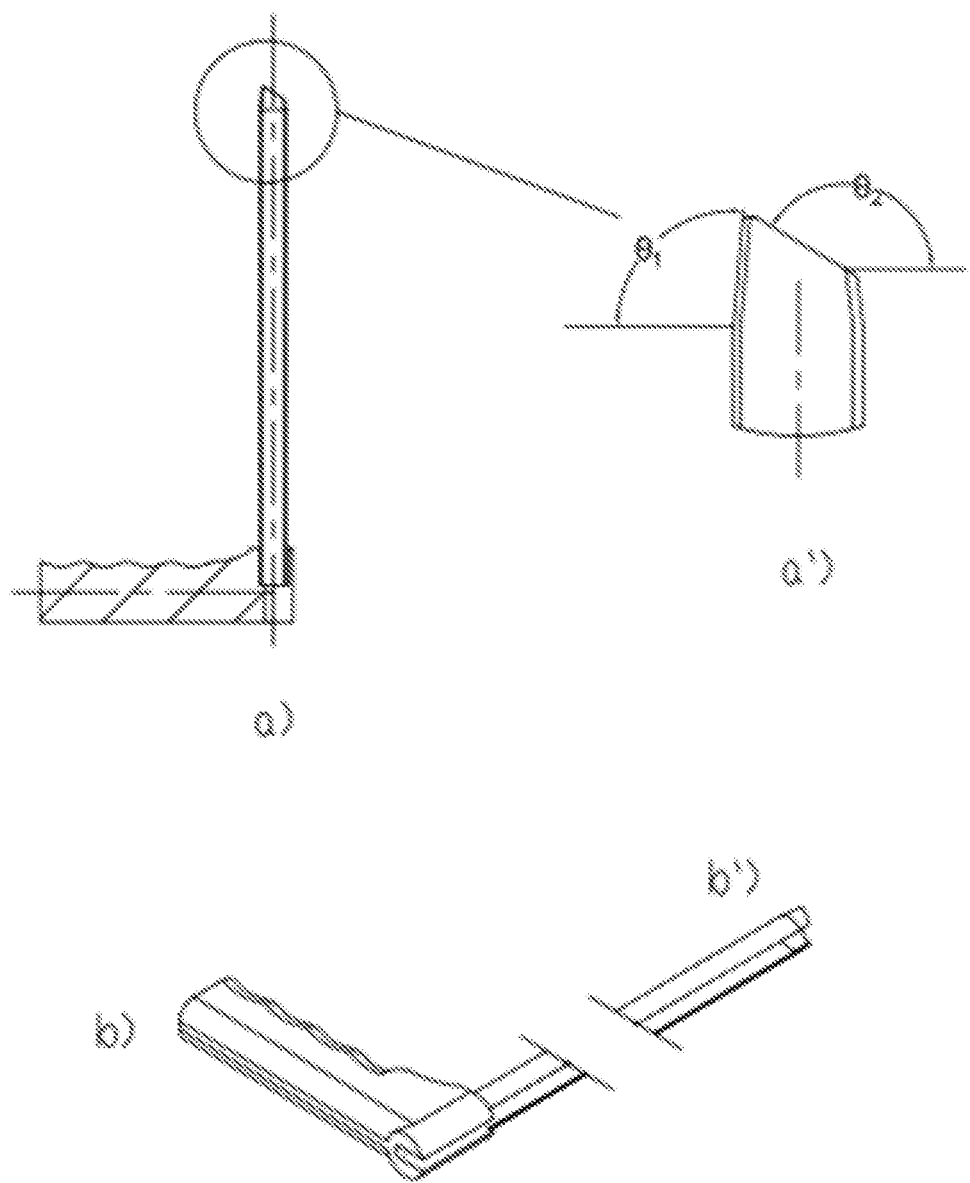
FIG. 35a: Axial section view of the extraction cannula of the removal instruments, axis of the L-handle coinciding with the bevel of the distal portion.
FIG. 35b: Detail view of the proximal portion of the extraction cannula, focused on the L-handle and its final slot.

2. Extraction cannula: Corresponds to a piece of cylindrical section with a diameter equivalent to the greatest height of the disc space and that along the entire length of its medial face, with respect to the patient's mid-sagittal plane, has a slot whose diameter allows for the free entry of the cylindrical portion of the extraction rod (FIG. 35*b*, *b'*). It has a tip with a conical reduction and a bevel with an axis perpendicular to the middle sagittal plane of the instrument (FIG. 35*a*, *a'*). This bevel facilitates the incorporation of the instrument into the disc space, which in turn facilitates the insertion of the AAD into its core once the closure system that secures its geometry has been broken. In its proximal pole, this cannula is provided with a handle whose medial axis is perpendicular to the middle axis of the instrument. Once inside, the extraction rod, together with the AAD already caught at its tip, can be extracted with absolute protection of the neural elements contained in the canal.

The invention claimed is:

1. An annular assistance device (AAD) for its positioning in a disc space between vertebrae of a spinal unit, comprising:
   a semi-rigid ring of non-uniform height, having a variable geometry that stabilizes at its final working position in a form of a cardioid; said cardioid having two lateral poles, distal and proximal in relation to an operator, and two perimeter portions, one anterior and one posterior; wherein said poles serve as anchor points for a closing element; and wherein supporting ribs are projected in a centripetal manner from said perimeter portions;

fastening spikes at ends of the supporting ribs;
an elongated closure element placed on a major or transverse axis of the semi-rigid ring that ensures, by means of its traction, a final geometric configuration, once housed inside the disc space; and
a positioning element that rests temporarily on the distal pole of the semi-rigid ring to control its positioning;
wherein a posterior section of the distal pole of the semi-rigid ring has two slots located between a base of a most distal posterior supporting rib and the anchor point for the closing element; and
wherein the positioning element is made from a resistant polymer that links to the distal pole of the semi-rigid ring by entering, loosely, by one of the slots and exiting through an other one of the slots.

2. The annular assistance device, according to claim 1, wherein in its final architectural configuration, the semi-rigid ring has a sagittal section with a convex outer surface in its ventral and lateral aspect and is concave in its posterior aspect.

3. The annular assistance device according to claim 2, wherein the semi-rigid ring is concave in its interior aspect.

4. The annular assistance device, according to claim 2, wherein in a sagittal section, upper and lower edges of the semi-rigid ring are convex and congruent with a surface of a disc platform, through which it relates to an adjacent vertebra.

5. The annular assistance device according to claim 1, wherein the semi-rigid ring can change its geometry from a configuration of minimum interior space when folded around its transverse axis, to that of a cardioid with its major axis perpendicular to a mid-sagittal plane of a vertebral unit.

6. The annular assistance device according to claim 1, wherein the maximum height of the semi-rigid ring has a maximum height equal to an average distance between vertebrae adjacent to the disc space.

7. The annular assistance device according to claim 6, wherein the maximum height of the semi-rigid ring is minimally exceeded by the fastening spikes at the ends of the supporting ribs projected from the posterior perimeter portion.

8. The annular assistance device according to claim 1, wherein the elongated closure element is made from a biocompatible material and has a cylindrical section with its anterior and posterior ends truncated, the elongate closure element further comprising an inner duct that runs through the elongated closure element from its proximal end to a section of the elongated closure element that is inside the semi-rigid ring, wherein the elongated closure element crosses the major axis of the semi-rigid ring and is solidly anchored to the distal pole of the semi-rigid ring.

9. The annular assistance device according to claim 8, wherein the distal pole of the semi-rigid ring has an increase in thickness that defines a resistant anchor point in which there is an entry hole with a countersunk conical section with a gap; said gap serving as a unidirectional hook to accommodate and secure in its position a first portion of the elongated closure element.

10. The annular assistance device according to claim 8, wherein the elongated closure element presents a solid portion of a conical section with an increase in diameter that defines a unidirectional lock and that is anchored in the distal pole of the semi-rigid ring, without distorting its outer surface.

11. The annular assistance device according to claim 8, wherein the inner duct of the elongated closure element communicates with an inner space of the semi-rigid ring through a plurality of micro perforations.

12. The annular assistance device according to claim 1, wherein the proximal pole of the semi-rigid ring comprises a unidirectional book and a tubular exit hole for the elongated closure element, said tubular exit hole allows the elongated closure element to completely cross the semi-rigid ring and extend towards a place from where it is handled.

13. The annular assistance device according to claim 12, wherein elongated closure element comprises a section having locking elements in its ventral face, said locking elements functioning as a unidirectional lock for fixing said elongated closure element to the semi-rigid ring.

14. The annular assistance device according to claim 13, wherein between the locking elements is a space greater than a distance that separates the unidirectional hook at the proximal pole of the semi-rigid ring from the tubular exit hole thereof.

15. The annular assistance device, according to claim 13, wherein the elongated closure element presents marks indicating that a last locking element is captured in the unidirectional hook of the proximal pole of the semi-rigid ring; said marks being arranged in an extension of the elongated closure element near the operator.

16. The annular assistance device according to claim 13, wherein the elongated closure element has a diameter reduction between each of its locking elements; said diameter reduction defining a structural weakness point.

17. The annular assistance device according to claim 13, wherein the section with locking elements of the elongated closure element comprises a first distal end, and a gap whose geometry and tolerance define the unidirectional hook for locking elements.

18. The annular assistance device according to claim 17, wherein the tubular exit hole of the semi-rigid ring has a tolerance immediately proximal to the unidirectional hook of the locking elements that, after a rotation of the elongated closure element, cuts it just outside the semi-rigid ring.

19. The annular assistance device according to claim 12, wherein a surface of the proximal pole of the semi-rigid ring presents two holes, one upper and one lower with respect to the tubular exit hole of the elongated closure element, for receiving a tool for pushing the annular assistance device into the disc space.

20. The annular assistance device according to claim 12, wherein a surface of the proximal pole of the semi-rigid ring comprises a posterior perforation with respect to the tubular exit hole of the elongated closure element, whose longitudinal axis leads to the unidirectional hook.

21. The annular assistance device according to claim 1, wherein the supporting ribs projecting from the posterior perimeter portion of the semi-rigid ring comprise securing slots whose dimension is coincident with an outer diameter of a body of the elongated closure element.

22. The annular assistance device, according to claim 21, wherein the fastening spikes are arranged at the ends of the posterior supporting ribs in such a way that, when the elongated closure element is housed in the securing slots located in its meridian plane, the fastening spikes protrude beyond an upper and lower limit of the semi-rigid ring.

23. The annular assistance device according to claim 1, made from a biocompatible, osteoinductive and radiolucent material, with or without shape memory, and having a stable structure and behavior at body temperature, in addition to inserts of osteoinductive metal on the spikes of the posterior supporting ribs.

24. A procedure for placing an annular assistance device (ADD) into the a disc space between vertebrae of a spinal unit, said procedure comprising the steps of"
providing said annular assistance device comprising: a semi-rigid ring of non-uniform height, having a variable geometry that stabilizes at its final working position in a form of a cardioid; said cardioid having two lateral poles, distal and proximal in relation to an operator, and two perimeter portions, one anterior and one posterior; wherein said poles serve as anchor points for a closing element; and wherein supporting ribs are projected in a centripetal manner from said perimeter portions;
fastening spikes at ends of the supporting ribs;
an elongated closure element placed on a major or transverse axis of the semi-rigid ring that ensures, by means of its traction, a final geometric configuration, once housed inside the disc space; and
a positioning element that rests temporarily on the distal pole of the semi-rigid ring to control its positioning;
wherein a posterior section of the distal pole of the semi-rigid ring has two slots located between a base of a most distal posterior supporting rib and the anchor point for the closing element; and
wherein the positioning element is made from a resistant polymer that links to the distal pole of the semi-rigid ring by entering, loosely, by one of the slots and exiting through an other of the slots;
arranging the elongated closure element of the annular assistance device on a transverse axis of the semi-rigid ring of the annular assistance device by introducing the elongated closure element, first through an entry hole in the distal pole of the semi-rigid ring, and then pulling the elongated closure element from an inside of the semi-rigid ring through an exit slot of the proximal pole, thus allowing to secure a unidirectional lock of a distal end of the elongated closure element and to hook said unidirectional lock to secure the elongated closure element in the proximal pole of the semi-rigid ring;
inserting the positioning element of the annular assistance device into slots of the distal pole of the semi-rigid ring;
shortening to a minimum a minor axis of the semi-rigid ring, with its elongated closure element and its positioning element, to place them inside a solid capsule at a distal end of an insertion cannula whose shape allows it to act as a separation piece of the disc space, with its elements properly positioned in its core;
inserting the annular assistance device housed in the solid capsule in the disc space, using the a standard microsurgical approach route generated for resection of a lesion of the a nucleus pulposus, with endo- or exoscopic microsurgical discretion;
pulling the elongated closure element to obtain a final cardioid geometric configuration of the annular assistance device;
administering, through an inner canal of the elongated closure element, bioactive materials of clinical utility in an inner confined space of the annular assistance device, and
cutting off the end of the elongated closure element protruding from the semi-rigid ring with the annular assistance device in its correct working position.

25. A procedure for removing an annular assistance device (ADD) from a disc space between vertebrae of a spinal unit, said annular assistance device comprising:
a semi-rigid ring of non-uniform height, having a variable geometry that stabilizes at its final working position in a form of a cardioid; said cardioid having two lateral poles, distal and proximal in relation to an operator, and two perimeter portions, one anterior and one posterior; wherein said poles serve as anchor points for a closing element; and wherein supporting ribs are projected in a centripetal manner from said perimeter portions;
fastening spikes at ends of the supporting ribs;
an elongated closure element placed on a major or transverse axis of the semi-rigid ring that ensures, by means of its traction, a final geometric configuration, once housed inside the disc space; and
a positioning element that rests temporarily on the distal pole of the semi-rigid ring to control its positioning;
wherein a posterior section of the distal pole of the semi-rigid ring has two slots located between a base of a most distal posterior supporting rib and the anchor point for the closing element; and
wherein the positioning element is made from a resistant polymer that links to the distal pole of the semirigid ring by entering, loosely, by one of the slots and exiting through an other of the slots;
said procedure comprising the steps of:
a. destroying a locking element of the elongated closure element of the annular assistance device, by inserting an extraction rod, having a conical and striated tip placed at the end of it, that is sufficiently long for its handling from outside of a surgical field, through a posterior perforation with respect to a tubular exit hole of the elongated closure element, located at the proximal pole of the semi-rigid ring of the annular assistance device;
b. hooking the annular assistance device which, when disassembled, acquires a geometry in which its interior space can collapse until a bi-laminar section is acquired; and
c. removing the annular assistance device through a split tubular cannula that exposes its distal portion in the disc space by conveniently separating it to facilitate removal of the device.

* * * * *